United States Patent
Tamareselvy et al.

(10) Patent No.: US 8,840,870 B2
(45) Date of Patent: Sep. 23, 2014

(54) POLYMERS AND COMPOSITIONS

(75) Inventors: Krishnan Tamareselvy, Brecksville, OH (US); Pascal Staelens, Affligem (BE)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 39 days.

(21) Appl. No.: 13/819,875

(22) PCT Filed: Sep. 1, 2011

(86) PCT No.: PCT/US2011/050196
§ 371 (c)(1),
(2), (4) Date: Feb. 28, 2013

(87) PCT Pub. No.: WO2012/031113
PCT Pub. Date: Mar. 8, 2012

(65) Prior Publication Data
US 2013/0164242 A1    Jun. 27, 2013

Related U.S. Application Data

(60) Provisional application No. 61/379,488, filed on Sep. 2, 2010.

(51) Int. Cl.
*A61K 8/81*  (2006.01)
*A61Q 19/00* (2006.01)
*A61Q 1/10*  (2006.01)
*A61Q 5/06*  (2006.01)

(52) U.S. Cl.
CPC ....... *A61K 8/8152* (2013.01); *A61K 2800/5424* (2013.01); *A61Q 5/06* (2013.01); *A61Q 19/00* (2013.01); *A61Q 1/10* (2013.01)
USPC .................... 424/70.7; 424/70.16; 424/78.02; 424/78.03

(58) Field of Classification Search
None
See application file for complete search history.

(56) References Cited

U.S. PATENT DOCUMENTS 3,726,288 A      4/1973  Nowak et al.
2007/0179078 A1  8/2007  Collin et al.

FOREIGN PATENT DOCUMENTS

WO    01/76552 A2    10/2001

*Primary Examiner* — Bethany Barham
*Assistant Examiner* — Randeep Singh
(74) *Attorney, Agent, or Firm* — Thoburn T. Dunlap

(57) ABSTRACT

The present invention relates to hair care and personal care compositions which contain an acrylic copolymer which is polymerized in the presence of at least two different classes of crosslinking monomers. The polymer functions both as a fixative/film former and a thickening agent for hair styling and personal care compositions in which it is contained. The copolymer exhibits advantageous fixative, film forming and rheological gel properties.

29 Claims, No Drawings

POLYMERS AND COMPOSITIONS

CROSS REFERENCE TO RELATED APPLICATION

This application claims priority from PCT Application Serial No. PCT/US2011/050196 filed on Sep. 1, 2011, which claims the benefit of U.S. Provisional Application No. 61/379,488 filed on Sep. 2, 2010.

TECHNICAL FIELD

In one aspect, the present invention relates to an acrylic copolymer wherein the copolymer is suitable both as a hair fixative/film former and a thickening agent in hair styling and personal care compositions. In another aspect, the invention relates to a hair styling gel composition comprising an acrylic copolymer, water and a neutralizing agent. The acrylic copolymer is polymerized in the presence of at least two different classes of crosslinking monomers. A further aspect of the invention relates to the formation of clear, rheologically stable, aqueous fixative gel compositions containing an acrylic based crosslinked copolymer, and optionally various components that are substantially insoluble materials requiring suspension.

BACKGROUND OF THE INVENTION

Most commercial, hair setting compositions include film forming polymers (fixatives), viscosity increasing polymers, and polymer modifiers, in addition to solvents, co-solvents, and cosmetic adjuvants, such as preservatives, color, fragrance, and the like. The amount of fixative polymer present in a particular hair setting composition can vary in the range of about 0.2 to about 10 weight percent, depending on the attributes desired during application and the function of the product. See, for example, Ch. 30, *Harry's Cosmeticology*, 8th Ed., M. J. Rieger, Ph.D. (ed.), 666-667, Chemical Publishing Co., Inc., New York, N.Y. (2000).

A common type of hair setting composition contains an aqueous based gel containing the fixative polymer which when applied to the hair "fixes" the hair in a desired configuration upon drying. The fixative polymer is deposited on the individual hair filaments as a thin film which encases the hair filaments tending to keep the hair in the configuration in which it has been set. In addition, in places where hair filaments overlap and touch the fixative acts as an adhesive to bind the hair filaments together, helping to hold the desired set.

In order to be effective, the fixative polymer must meet a number of rigid requirements. The films derived from these polymers should be flexible and yet possess strength and elasticity. They should display good adhesion to the hair so as to avoid dusting or flaking off over extended periods of time or when the hair is subjected to stresses such as brushing or combing. Moreover, polymeric fixative films should not interfere with the brushing or combing of the hair, and should remain free of tack or stickiness under humid conditions. Applied fixative films should also be transparent, glossy, maintain clarity upon aging, and be easily removable when washing with a hair cleanser and water.

Also of importance are the aesthetic characteristics and appearance of hair setting compositions before, during, and after application to hair. In addition, the product viscosity should be non-runny to avoid dripping from opened and inverted product containers such as tubes and jars and from the fingers prior to application to the hair. Product clarity is preferably substantially transparent or clear in order to obtain a "clean" product appearance. The product should be shear thinning for easy application, have a smooth texture, a non-tacky feel, and be able to dry relatively quickly on the hair.

Conventional polymeric hair styling or hair fixative polymers, well known in the art, include natural gums and resins and neutral and anionic polymers of synthetic origin. Some commercially available neutral and anionic polymers, which have been used as hair styling or fixative polymers include, for example, polyvinylpyrrolidone (PVP), polyvinylpyrrolidone/vinylacetate copolymer (PVP/VA), and acrylates/hydroxyesters acrylates copolymers (Rohm and Haas). Acrylates Copolymer (Balance CR, Akzo; Luviflex Soft, Luvimer 100P, and Luvimer Pro 55 marketed by BASF), AMP-Acrylates/Allyl Methacrylate Copolymer (Fixate™ G-100, Lubrizol Advanced Materials, Inc.), Polyacrylate-14 (Fixate™ Plus, Lubrizol Advanced Materials, Inc.), and Polyacrylate-2 crosspolymer (Fixate™ Superhold, Lubrizol Advanced Materials, Inc.) are other examples of anionic styling polymers. For example, U.S. Pat. No. 4,196,190 to Gehman, et al., discloses an acrylic hair fixative resin made via emulsion polymerization techniques containing between 10 to 30 weight % of an alkyl acrylate, between 41 to 60 weight % of methyl methacrylate, between 5 to 20 weight % of hydroxyethyl methacrylate, and between 10 to 30 weight % of methacrylic acid. Acrylates/acrylamide copolymers (Ultimer® CG 700 from Nalco Company), Acrylic Acid/VP Crosspolymer (Ultrathix™ P-100, ISP), ethyl and butyl esters of polyvinyl methyl ether/maleic anhydride copolymer (PVM/MA) (GANTREZ®, ISP), and a copolymer of vinylpyrrolidone/acrylic acid/lauryl methacrylate (STYLEZE™ 2000, ISP) are other examples.

One of the shortcomings of conventional fixative polymers is that they generally do not provide significant thickening or contribute significant rheological properties at practical use concentrations. Consequently, conventional hair setting compositions typically require, in addition to the hair setting or fixative polymer, the addition of one or more viscosity increasing thickeners or gellants to provide a more convenient or pleasing product or to cause the preparation to be retained on the hair while the carrier vehicle evaporates. Typical thickeners or gellants that have been employed in the art include natural gums, synthetic polymers and other rheology modifying additives, such as emulsifiers, waxes, and the like, to achieve the desired rheological gel properties. A few examples of synthetic and natural polymers that have been used as gellants in commercial hair fixative products include Carbomers (crosslinked polyacrylic acid polymers) and hydrophobically modified derivatives thereof, sold under the registered trademark Carbopol®, such as Carbopol® 980 polymer, Carbopol® 940 polymer, Carbopol® Ultrez 10 polymer, Carbopol® Ultrez 21 polymer, Carbopol® Ultrez 20 polymer, Carbopol® ETD 2020 polymer, and the like marketed by Lubrizol Advanced Materials, Inc., hydrophobically modified cellulose, xanthan gum and hydrophobically modified, alkali-swellable, emulsion polymers (HASE polymers).

However, conventional anionic hair setting and hair fixative polymers frequently are incompatible with the rheology modification agent or gellant, resulting in loss of viscosity, lack of gel product clarity, unpleasant texture properties (e.g., gelatin like, crumbly, gooey, slimy, runny and/or stringy texture profiles) and loss of shear thinning rheology. Polymers possessing shear thinning rheology will, upon exposure to shear stress, show a decrease in viscosity, allowing easier delivery and application to and on the target substrate. Furthermore, upon removal of the shear stress, these compositions will rapidly recover to their initial viscosity. One method of applying a hair styling gel entails placing the hair gel in the hands, distributing the gel over the hands (applying shear) to form an even film, and then applying the film by passing the hands through the hair. This property allows such compositions to be easily transferred from fingers and palms during application to the hair. Consequently, hair fixative polymers suitable for all around use and ease of application, especially in gel formulations, may be limited primarily to neutral (i.e., uncharged, nonionic) polymers, such as PVP, and PVP/VA. However, these nonionic polymers are marginally effective in retaining a hair style or curl, impart a tacky, sticky feel to hair at conditions of relatively high humidity, and a raspy, harsh feel to dry hair. Additionally, the need for viscosity thickening or gellant additives increases the risk of leaving an unwanted residue or a dull film on the hair.

A prior art attempt to achieve a crosslinked acrylate polymer that is both a hair fixative and thickener is disclosed in U.S. Pat. No. 3,726,288 to Nowak, et al. However, the polymers disclosed are produced by an organic solvent based polymerization process using a toxic organic solvent (benzene) and, while thickening was achieved, hair fixative properties were weak (curl retention of less than 50% after 0.5 hours at 72° F. (about 22° C.) and 90% relative humidity).

Anionic polymers also have disadvantages, such as high water solubility, and therefore, low substantivity on hair fibers, resulting in low humidity resistance and generating a crust and flaking due to easy elimination from the hair by brushing and combing.

There is an ongoing need and desire, therefore, for a rheology modifying, hair setting polymer providing both thickening and effective hair fixative properties. In addition, there is a need for an anionic styling polymer that is compatible with anionic rheology modifiers or thickeners that also provides esthetically pleasing smooth gel appearance including clarity, hair fixative properties and good shear thinning rheology properties. Surprisingly, it has now been found that anionic acrylic copolymers polymerized in the presence of two different classes of crosslinking monomers and/or having a specific viscosity ($\eta_{sp}$) ranging from about 1 to 8 (measured in DMSO solvent) offer aesthetically pleasing smooth gel formulations with high clarity in addition to hair styling efficacy and stiffness. These crosslinked acrylic polymers overcome the disadvantages (unacceptable and unpleasant fixative, gel, and aesthetic properties) associated with the current commercially available hair styling polymers.

SUMMARY OF THE INVENTION

In one aspect, embodiments of the present invention relate to acrylic copolymers crosslinked with at least two different classes of crosslinking monomers that are suitable as fixatives and as film formers on keratinous substrates in hair styling and personal care compositions.

In another aspect, an embodiment of the invention relates to acrylic copolymers crosslinked with at least two different classes of crosslinking monomers and having a specific viscosity ($\eta_{sp}$) ranging from about 1 to 8 (measured in DMSO solvent) that are suitable as fixatives in a hair styling composition or as a film former in a personal care composition.

In still another aspect, an embodiment of the invention relates to a hair styling composition or a personal care composition comprising an acrylic copolymer crosslinked with at least two different classes of crosslinking monomers, water, and a neutralizing agent.

In a further aspect, an embodiment of the invention relates to a hair styling composition or a personal care composition comprising an acrylic copolymer crosslinked with at least two different classes of crosslinking monomers, the copolymer having a specific viscosity ($\eta_{sp}$) ranging from about 1 to 8 (measured in DMSO solvent), water, and a neutralizing agent.

In a still further aspect, an embodiment of the invention relates to a hair styling composition comprising an aqueous based gel of a single material of an acrylic copolymer crosslinked with at least two different classes of crosslinking monomers, which material serves both as a fixative for the hair and a thickener for the gel.

In a still further aspect, an embodiment of the invention relates to a personal care composition comprising an acrylic copolymer crosslinked with at least two different classes of crosslinking monomers, which copolymer serves both as a film former on the skin and a thickener for the gel.

In a further aspect, an embodiment of the invention relates to a hair styling gel composition or a personal care composition comprising an acrylic copolymer crosslinked with at least two different classes of crosslinking monomers, an auxiliary rheology modifier, water, and a neutralizing agent.

In another aspect, embodiments of the invention relate to a hair styling gel composition comprising an acrylic copolymer crosslinked with at least two different classes of crosslinking monomers having superior fixative (e.g., hold, stiffness, elasticity, volume, and humidity resistance) and gel properties (e.g. clarity, viscosity, shear thinning ability, yield, suspension stability, short flow, and texture).

In still another aspect, embodiments of the invention relate to a film forming polymer composition suitable for use in cosmetic and skin care applications.

The hair styling gel composition and the personal care composition of the present invention comprises three major components: A) a crosslinked acrylic copolymer, B) water, and C) a neutralizer to neutralize the acid groups on the crosslinked acrylic copolymer backbone. The crosslinked acrylic copolymer of the invention is polymerized from a monomer composition comprising:

a) from about 10% to about 80% by weight of a first monomeric component selected from one or more monoethylenically unsaturated monomers containing at least one carboxylic acid group;

b) from about 90% to about 15% by weight of a second monoethylenically unsaturated monomeric component selected from at least one linear or branched $C_1$ to $C_5$ alkyl ester of (meth)acrylic acid, at least one $C_1$ to $C_5$ hydroxyalkyl ester of (meth)acrylic acid, and mixtures thereof;

c) from about 0.01% to about 5% by weight of crosslinking component chosen from a first polyunsaturated crosslinking monomer and a second polyunsaturated crosslinking monomer, wherein said first crosslinking monomer is selected from at least one (meth)acrylic acid ester of a polyol and said second crosslinking monomer is selected from at least one allyl ether of a polyol; and optionally d) from about 1% to about 35% by weight of at least one other monoethylenically unsaturated monomer component different from monomeric components a), b), and c) wherein all monomer weight percentages are based on the weight of the total monomer composition.

In one embodiment of the invention, the hair styling gels and personal care compositions have a pH value ranging from about 4.0 to about 12.0.

In one embodiment of the invention, the hair styling gels have a viscosity of about 7,000 mPa·s to about 25,000 mPa·s.

In one embodiment of the invention, the hair styling gels have a clarity value (percent light transmittance, % T) of ≥60% in one aspect, of ≥70% in another aspect, and ≥80% in a further aspect, as measured on a 4 wt. % mucilage of total polymer solids of the crosslinked acrylic polymer neutralized to a pH of 7.0.

The crosslinked acrylic copolymers, fixative compositions, and personal care compositions of the present invention may suitably comprise, consist of, or consist essentially of the components, elements, and process delineations described herein. The invention illustratively disclosed herein suitably may be practiced in the absence of any element which is not specifically disclosed herein.

Unless otherwise stated, all percentages, parts, and ratios expressed herein are based upon weight of the total compositions of the present invention, and all weights are expressed on the basis of 100 percent active ingredients.

As used herein, the term "(meth)acrylic" acid is meant to include both acrylic acid and methacrylic acid. Similarly, the term "alkyl(meth)acrylate" as used herein is meant to include alkyl acrylate and alkyl methacrylate.

The terms "hair styling", "hair setting" and "hair fixative" as commonly understood in the hair care art, and as used herein, refer collectively to hair setting agents that are hair fixatives and film formers and which are topically applied to the hair to actively contribute to the ease of styling and/or holding of a hair set, and to maintain the restylability (multiple reshaping) of the hair set. Hence, the present hair setting compositions can include hair styling, hair fixative, and hair grooming products that conventionally are applied to the hair (wet or dry) in the form of a gel to leave the hair setting agent in contact on the hair for some period until removed, as by washing.

The term "personal care composition" as used herein includes, without being limited thereto, cosmetics, skin care, toiletries, cosmeceuticals, beauty aids, insect repellents, sunscreens, anti-itch gels, hand sanitizing compositions, and the like applied to the body, including the skin, hair, scalp, and nails of humans and animals.

DESCRIPTION OF EXEMPLARY EMBODIMENTS

Exemplary embodiments in accordance with the present invention will be described. Various modifications, adaptations or variations of the exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

The present hair styling and personal care compositions contain a film forming crosslinked acrylic copolymer, an aqueous carrier and a neutralizing agent. The crosslinked acrylic copolymer is useable as the single component fixative or film former and thickener. Optionally, and auxiliary thickener and/or fixative resin can be included in the hair styling or personal care composition. The present hair styling and personal care compositions overcome problems and disadvantages associated with compositions which contain traditional anionic based fixative resins, and provide improved fixative (e.g., hold, elasticity, humidity resistance, resistance to flaking), rheological (e.g., viscosity, yield value, shear thinning), gel (e.g., short flow), and aesthetic (e.g., clarity, texture) properties.

Crosslinked Acrylic Copolymers

The film forming crosslinked acrylic copolymers useable as the single component fixative and thickener is polymerized from a monomer composition comprising three different monomer components, a), b), c), and an optional fourth monomer component d). The first monomer component a) is selected from one or more monoethylenically unsaturated monomers containing at least one carboxylic acid group.

Exemplary monoethylenically unsaturated monomers containing at least one carboxylic acid group which are set forth under the first monomer component a) include (meth) acrylic acid, itaconic acid, citraconic acid, maleic acid, fumaric acid, crotonic acid, aconitic acid, and mixtures thereof.

In one aspect of the invention, the amount of the at least one carboxylic acid group containing monomer set forth under the first monomer component ranges from about 10% to 80% by weight in one aspect, from about 20% to about 70% by weight in another aspect, and from about 35% to about 65% by weight in a further aspect of the invention, based upon the total weight of the monomers in the polymerizable monomer composition.

The second monomer component b) is selected from at least one monoethylenically unsaturated monomer containing at least one linear or branched $C_1$ to $C_5$ alkyl ester of (meth)acrylic acid, at least one $C_1$ to $C_5$ hydroxyalkyl ester of (meth)acrylic acid, and mixtures thereof.

Exemplary linear or branched $C_1$ to $C_5$ alkyl(meth)acrylate and hydroxyalkyl(meth)acrylate monomers set forth under the second monomer component include methyl(meth)acrylate, ethyl (meth)acrylate, n-propyl(meth)acrylate, iso-propyl (meth)acrylate, n-butyl (meth)acrylate, isobutyl(meth)acrylate, t-butyl (meth)acrylate, n-amyl (meth)acrylate, iso-amyl (meth)acrylate, hydroxyethyl(meth)acrylate, hydroxypropyl (meth)acrylate, hydroxybutyl(meth)acrylate (butane diol mono(meth)acrylate), and mixtures thereof.

In one aspect of the invention, the alkyl and hydroxyalkyl (meth)acrylate monomers set forth under the second monomer component are utilized in an amount ranging from about 90% to about 15% by weight, from about 80% to about 25% by weight in another aspect, and from about 65% to about 35% by weight in still another aspect of the invention, based upon the total weight of the monomers in the polymerizable monomer composition.

The third monomer component c) comprises a mixture of crosslinking monomers selected from at least two different polyunsaturated monomer types or classes. The first crosslinking monomer is selected from at least one polyfunctional acrylate having at least two polymerizable ethylenically unsaturated double bonds. The term "polyfunctional acrylate" refers to acrylate esters of organic polyols wherein the organic polyol is esterified by reacting it with (meth) acrylic acid. The polyfunctional acrylate can contain 2 to 6 polymerizable ethylenically unsaturated double bonds. Suitable polyols for the esterification reaction can contain 2 to 12 carbon atoms and have at least two hydroxyl groups. The polyol can be linear and branched or cyclic. Exemplary polyols suitable for esterification include, but are not limited to, alkylene glycols containing 2 to 5 carbon atoms, polyalkylene glycol dimers and trimers, trimethylolethane and dimers thereof, trimethylolpropane and dimers thereof, triethylolpropane and dimers thereof, tetramethylolmethane (pentaerythritol), dipentaerythritol, and 1,4-cyclohexanediol.

Exemplary polyfunctional acrylates include, but are not limited to, ethylene glycol di(meth)acrylate, triethylene glycol di(meth)acrylate, 1,3-butylene glycol di(meth)acrylate, 1,4-butylene glycol di(meth)acrylate, 1,6-hexanediol di(meth)acrylate, neopentyl glycol di(meth)acrylate, 1,9-nonanediol di(meth)acrylate, trimethylolpropane tri(meth) acrylate, trimethylolethane tri(meth)acrylate, tetramethylolmethane tri(meth)acrylate, ditrimethylolpropane tetra(meth)

acrylate, tetramethylolmethane tetra(meth)acrylate, pentaerythritol tetra(meth)acrylate; dipentaerythritol hexa(meth)acrylate, 1,4-cyclohexanediol dimethyacrylate, and mixtures thereof.

The second crosslinking monomer is selected from at least one polyalkenyl polyether having at least two polymerizable ethylenically unsaturated double bonds. The term "polyalkenyl polyether" refers to alkenyl ethers of organic polyols wherein the organic polyol is etherified by reacting it with alkenyl halide, such as allyl chloride or allyl bromide. The polyalkenyl polyether (e.g., polyallyl polyether) can contain 2 to 8 polymerizable ethylenically unsaturated double bonds. Suitable polyols for the etherification reaction can contain 2 to 12 carbon atoms and have at least two hydroxyl groups. The polyol can be linear and branched or cyclic (e.g., monosaccharides and polysaccharides containing 1 to 4 saccharide units). Exemplary polyols suitable for etherification include, but are not limited to, glucose, galactose, fructose, sorbose, rhamnose, sucrose, arabinose, maltose, lactose, raffinose, pentaerythritol, dipentaerythritol, trimethylolethane and dimers thereof, trimethylolpropane and dimers thereof, and triethylolpropane and dimers thereof. Additional polyols suitable for the etherification are disclosed in U.S. Pat. No. 2,798,053, the disclosure of which is hereby incorporated by reference.

Exemplary polyalkenyl polyethers include, but are not limited to, polyallyl ethers of sucrose having from 2 to 8 alkyl groups per molecule, pentaerythritol diallyl ether, pentaerythritol triallyl ether, and pentaerythritol tetraallyl ether; trimethylolpropane diallyl ether, trimethylolpropane triallyl ether, and mixtures thereof.

In one aspect of the invention, the mixture of crosslinking monomers (first and second crosslinking monomer components) set forth under the third monomer component is present in an amount ranging from about 0.01% to about 5% by weight, from about 0.03 to about 3% by weight in another aspect, and from about 0.05 to about 1% by weight in a further aspect, based upon the total weight of the monomers in the polymerizable monomer composition. In one aspect of the invention, the weight ratio of the first crosslinking monomer to the second crosslinking monomer in the polymerizable monomer mixture ranges from about 1:99 to about 99:1, from about 1:9 to about 9:1 in another aspect, from about 2:8 to about 8:2 in a further aspect, from about 3:7 to about 7:3 in still another aspect, from about 4:6 to about 6:4 in another aspect, and from about 1:1 in still another aspect.

The optional fourth monomer component d) is a monoethylenically unsaturated monomer different from monomer components a), b), and c). In one aspect of the invention, monomer component d) is selected from one or more monomers represented by the formulas:

$$CH_2=C(R)C(O)OR^1, \qquad (d1)$$

wherein R is selected from hydrogen or methyl; and $R^1$ is selected from $C_6$-$C_{10}$ alkyl, $C_6$ to $C_{10}$ hydroxyalkyl, —(CH$_2$)$_2$OCH$_2$CH$_3$, and —(CH$_2$)$_2$C(O)OH

$$CH_2=C(R)X, \qquad (d2)$$

wherein R is hydrogen or methyl; and X is selected from —C$_6$H$_5$, —CN, —C(O)NH$_2$, —NC$_4$H$_6$O, —C(O)NHC(CH$_3$)$_3$, —C(O)N(CH$_3$)$_2$, —C(O)NHC(CH$_3$)$_2$(CH$_2$)$_4$CH$_3$, and —C(O)NHC(CH$_3$)$_2$CH$_2$S(O)(O)OH;

$$CH_2=CHOC(O)R^1, \qquad (d3)$$

wherein $R^1$ is linear or branched $C_1$-$C_{18}$ alkyl; and

$$CH_2=C(R)C(O)OAOR^2, \qquad (d4)$$

wherein A is a divalent radical selected from —CH$_2$CH(OH)CH$_2$— and —CH$_2$CH(CH$_2$OH)—, R is selected from hydrogen or methyl, and $R^2$ is an acyl residue of a linear or branched, saturated or unsaturated $C_9$ to $C_{22}$ fatty acid.

Exemplary ethylenically unsaturated monomers set forth under formulas d1) to d4) of optional fourth monomeric component d) include ethyl diglycol(meth)acrylate, 2-carboxyethyl(meth)acrylate, n-hexyl(meth)acrylate, 2-ethylhexyl(meth)acrylate, octyl(meth)acrylate, decyl(meth)acrylate, 6-hydroxyhexyl(meth)acrylate, 10-hydroxydecyl(meth)acrylate, styrene, α-methyl styrene, acrylonitrile, methacrylonitrile, acrylamide, methacrylamide, N,N'-dimethylaminoacrylamide, t-butylacrylamide, t-octylacrylamide, N-vinyl pyrrolidone, 2-acrylamido-2-methylpropane sulfonic acid, vinyl acetate, vinyl propionate, vinyl butanoate, vinyl valerate, vinyl hexanoate, vinyl octanoate, vinyl nonanoate, vinyl decanoate, vinyl neodecanoate, vinyl undecanoate, vinyl laurate, ACE™ and (M)ACE™ monomer available from Hexion Specialty Chemicals, Inc., Columbus, Ohio; and mixtures thereof. The foregoing monomers are commercially available and/or can be synthesized by procedures well known in the art, or as described herein.

The ACE monomer (CAS No. 94624-09-06) is the reaction product of glycidyl t-decanoate (CAS No. 71206-09-2) and acrylic acid. The (M)ACE Monomer is synthesized by reacting glycidyl t-decanoate and methacrylic acid.

Monomers set forth under formula d4) of the optional fourth monomer component can be synthesized via esterification by reacting glycidol with a $C_{10}$ to $C_{22}$ fatty acid to obtain the glycidyl ester of the respective fatty acid(s). The so-formed glycidyl ester can in turn be reacted through its epoxy functionality with the carboxyl moiety of (meth)acrylic acid to obtain a preformed monomer. Alternatively, the glycidyl ester of the fatty acid can be added to the polymerization mixture comprising the previously described monomers and reacted in situ with a portion of the one or more ethylenically unsaturated monomers containing at least one carboxylic acid group described under monomer component a), subject to the proviso that the reactant stoichiometry is designed such that only a portion of the carboxyl groups are reacted. In other words, sufficient acid functionality must be retained to serve the purpose of the present invention.

In one aspect of the invention, suitable glycidyl esters for forming the preformed and in situ formed monomer components described under formula iv) are disclosed in U.S. Pat. No. 5,179,157 (column 13). The relevant disclosure of which is herein incorporated by reference. A glycidyl ester of neodecanoic acid and isomers thereof is commercially available under the trade name Cardura™ E10P from Hexion Specialty Chemicals, Inc.

In one aspect of the invention, monomers set forth under formulas d1) to d4) of the optional fourth monomer component d) are utilized in an amount ranging from about 0% to about 35% by weight, from about 1% to about 30% by weight in another aspect, from about 2% to about 15% by weight in still another aspect, and from about 5% to about 10% by weight in a further aspect, based upon the total weight of the monomers in the polymerizable monomer composition.

As one of ordinary skill in the art will readily recognize the amounts of each of the first, second, third, and optional fourth monomer components set forth herein will be selected from the disclosed ranges such that the sum of each of the monomer components in the polymerizable monomer compositions is equal to 100 wt. %.

Crosslinked Acrylic Copolymer Synthesis

The acrylic copolymers of the invention can be synthesized via emulsion polymerization techniques well known in the art. A mixture of the first, second, third, and optionally the fourth monomer components is emulsified in an aqueous phase. The emulsified monomers are polymerized in the presence of a suitable free radical forming initiator to provide an emulsion of acrylic copolymers useful as the fixative/film former and thickener component in the hair styling/personal care compositions of the invention.

If desired, the acrylic copolymers useful in the hair styling compositions and personal care compositions of the invention can be prepared from a monomer mixture comprising one or more chain transfer agents. The chain transfer agent can be any chain transfer agent which reduces the molecular weight of the polymers of the invention. Suitable chain transfer agents include, but are not limited to, thio and disulfide containing compounds, such as $C_1$-$C_{18}$ alkyl mercaptans, mercaptocarboxylic acids, mercaptocarboxylic esters, thioesters, $C_1$-$C_{18}$ alkyl disulfides, aryldisulfides, polyfunctional thiols such as trimethylolpropane-tris-(3-mercaptopropionate), pentaerythritol-tetra-(3-mercaptopropionate), pentaerythritol-tetra-(thioglycolate), and pentaerythritol-tetra-(thiolactate), dipentaerythritol-hexa-(thioglycolate), and the like; phosphites and hypophosphites; haloalkyl compounds, such as carbon tetrachloride, bromotrichloromethane, and the like; and catalytic chain transfer agents such as, for example, cobalt complexes (e.g., cobalt (II) chelates).

In one aspect of the invention, the chain transfer agent is selected from octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, and dodecyl thioglycolate.

When utilized, the chain transfer agent can be present in an amount ranging from about 0.1% to 10% by weight, based on the total monomer mixture weight.

The emulsion polymerization can be carried out in a batch process, in a metered monomer addition process, or the polymerization can be initiated as a batch process and then the bulk of the monomers can be continuously metered into the reactor (seed process). Typically, the polymerization process is carried out at a reaction temperature in the range of about 20 to about 99° C.; however, higher or lower temperatures can be used. To facilitate emulsification of the monomer mixture, the emulsion polymerization is carried out in the presence of at least one surfactant. In one embodiment, the emulsion polymerization is carried out in the presence of surfactant ranging in the amount of about 1% to about 10% by weight in one aspect, from about 3% to about 8% in another aspect, and from about 3.5% to about 7% by weight in a further aspect, based on a total emulsion weight basis. The emulsion polymerization reaction mixture also includes one or more free radical initiators which are present in an amount in the ranging from about 0.01% to about 3% by weight based on total monomer weight. The polymerization can be performed in an aqueous or aqueous alcohol medium. Surfactants for facilitating the emulsion polymerization include anionic, nonionic, amphoteric, and cationic surfactants, as well as mixtures thereof. Most commonly, anionic and nonionic surfactants can be utilized as well as mixtures thereof.

Suitable anionic surfactants for facilitating emulsion polymerizations are well known in the art and include, but are not limited to, sodium lauryl sulfate, sodium dodecyl benzene sulfonate, sodium ($C_6$-$C_{16}$) alkyl phenoxy benzene sulfonate, disodium ($C_6$-$C_{16}$) alkyl phenoxy benzene sulfonate, disodium ($C_6$-$C_{16}$) di-alkyl phenoxy benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like.

Nonionic surfactants suitable for facilitating emulsion polymerizations are well known in the polymer art, and include, without limitation, linear or branched $C_8$-$C_{30}$ fatty alcohol ethoxylates, such as capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and, behenyl alcohol ethoxylate; alkylphenol alkoxylates, such as octylphenol ethoxylates; and polyoxyethylene polyoxypropylene block copolymers, and the like. Additional fatty alcohol ethoxylates suitable as non-ionic surfactants are described below. Other useful nonionic surfactants include $C_8$-$C_{22}$ fatty acid esters of polyoxyethylene glycol, ethoxylated mono- and diglycerides, sorbitan esters and ethoxylated sorbitan esters, $C_8$-$C_{22}$ fatty acid glycol esters, block copolymers of ethylene oxide and propylene oxide, and combinations thereof. The number of ethylene oxide units in each of the foregoing ethoxylates can range from 2 and above in one aspect, and from 2 to about 150 in another aspect.

Exemplary free radical initiators include, but are not limited to, water-soluble inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil soluble, free radical producing agents, such as 2,2'-azobisisobutyronitrile, and the like, and mixtures thereof. Peroxides and peracids can optionally be activated with reducing agents, such as sodium bisulfite, sodium formaldehyde, or ascorbic acid, transition metals, hydrazine, and the like. Particularly suitable free-radical polymerization initiators include water soluble azo polymerization initiators, such as 2,2'-azobis(tert-alkyl) compounds having a water solubilizing substituent on the alkyl group. Preferred azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine)dihydrochloride), and Vazo® 68 (4,4'-azobis(4-cyanovaleric acid)).

Optionally, other emulsion polymerization additives and processing aids which are well known in the emulsion polymerization art, such as auxiliary emulsifiers, solvents, buffering agents, chelating agents, inorganic electrolytes, polymeric stabilizers, biocides, and pH adjusting agents can be included in the polymerization system.

In one aspect, an auxiliary emulsifying aid selected from an ethoxylated $C_{10}$ to $C_{22}$ fatty alcohol (or their mixtures) can be added to the polymerization medium. In one aspect, the fatty alcohol contains from about 5 to about 250 moles of ethoxylation, from about 8 to 100 moles in another aspect, and from about 10 to 50 moles in a further aspect. Exemplary ethoxylated fatty alcohols include lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and behenyl alcohol ethoxylate. In another aspect, suitable ethoxylated fatty alcohols include Ceteth-20, Ceteareth-20, and Steareth-20, Behenth-25, and mixtures thereof.

If employed, the amount of ethoxylated fatty alcohol can range from about 0.1% to 10% by weight in one aspect, from about 0.5% to about 8% by weight in another aspect, and from about 1% to about 5% by weight in a further aspect, based on the total weight percent of the monomers present in the polymerization medium.

In a typical emulsion polymerization, a mixture of the monomers is added to a first reactor under inert atmosphere to a solution of emulsifying surfactant (e.g., anionic surfactant) in water. Optional processing aids can be added as desired (e.g., auxiliary emulsifier(s)). The contents of the reactor are agitated to prepare a monomer emulsion. To a second reactor equipped with an agitator, an inert gas inlet, and feed pumps are added under inert atmosphere a desired amount of water and additional anionic surfactant and optional processing aids. The contents of the second reactor are heated with mixing agitation. After the contents of the second reactor reaches a temperature in the range of about 55 to 98° C., a free radical initiator is injected into the so formed aqueous surfactant solution in the second reactor, and the monomer emulsion from the first reactor is gradually metered into the second reactor over a period typically ranging from about one half to about six hours. The reaction temperature is controlled in the range of about 45 to about 95° C. After completion of the monomer addition, an additional quantity of free radical initiator can optionally be added to the second reactor, and the resulting reaction mixture is typically held at a temperature of about 45 to 95° C. for a time period sufficient to complete the polymerization reaction to obtain an emulsion of acrylic copolymer particles.

Hair Styling and Personal Care Compositions

While embodiments of the invention are described in terms of hair styling compositions, it is to be noted that the crosslinked acrylic copolymers of the invention as well as the ingredients and optional components disclosed herein can be formulated into personal care product as one of ordinary skill in the personal care formulation art can readily determine.

In one embodiment of the invention, hair styling and personal care compositions can be prepared by mixing the crosslinked acrylic copolymer in water and neutralizing the polymer with an alkaline material to a desired degree of neutralization. The amount of polymer utilized in the composition ranges from about 0.1 wt. % to about 15 wt. % in one aspect, from about 0.5 wt. % to about 10 wt. % in another aspect, and from about 1 wt. % to about 5 wt. % in a further aspect, based on the weight of the total components in the composition. All polymer weight percents are based upon 100 percent total active polymer solids (T.S.). The polymer can be neutralized to a pH ranging from about 4 to about 12 in one aspect, from about 5 to about 10 in another aspect, from 6 to about 9 in a further aspect, and from about 6.4 to about 7.5 in a still further aspect of the invention. The compositions made by this technique are of very high clarity and viscosity and are suitable for use as hair styling gels and as film formers in personal care compositions.

In another embodiment of the invention, an optional auxiliary anionic thickener can be incorporated into the single component fixative/thickener composition described above. In one aspect, the auxiliary anionic thickener is selected from carboxyl functional alkali-swellable and alkali-soluble thickeners (ASTs) produced by the free-radical polymerization of acrylic acid alone or in combination with other ethylenically unsaturated monomers. These polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule, wherein in one aspect the substituent is independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol. These polymers are more fully described in U.S. Pat. No. 5,087,445; U.S. Pat. No. 4,509,949; and U.S. Pat. No. 2,798,053 which are herein incorporated by reference.

In one aspect, the auxiliary AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980, 981, 984, 996, and 2050, available from Lubrizol Advanced Materials, Inc. In a further aspect, the auxiliary thickener is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl esters of acrylic acid or methacrylic acid. In one aspect, the monomers can be polymerized in the presence of a steric stabilizer such as disclosed in U.S. Pat. No. 5,288,814, which is herein incorporated by reference. Some of the foregoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020, and Pemulen® TR-1 and TR-2 from Lubrizol Advanced Materials, Inc.

Another class of auxiliary anionic rheology modifiers or thickeners suitable for use in the present invention includes the hydrophobically modified ASTs, commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid, 2-acrylamido-2-methylpropane sulfonic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843, which are herein incorporated by reference. In addition, an extensive review of HASE polymers is found in Gregory D. Shay, Chapter 25, "Alkali-Swellable and Alkali-Soluble Thickener Technology A Review", Polymers in Aqueous Media—Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. Commercially available HASE polymers are sold under the trade names, Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer) from Rohm & Haas, Aculyn® 28 (INCI Name: Acrylates/Beheneth-25 Methacrylate Copolymer) from Rohm & Haas, and Novethix™ L-10 (INCI Name: Acrylates/Beheneth-25 Methacrylate Copolymer) from Lubrizol Advanced Materials, Inc. Other thickeners are commercially available under the INCI designations Ammonium Acryloyldimethyltaurate/VP Copolymer, Ammonium Acryloyl Dimethyltaurate/Carboxyethyl Acrylate Crosspolymer, and Ammonium Acryloyldimethyltaurate/Beheneth-25 Methacrylate Crosspolymer.

In this embodiment, the amount of the auxiliary anionic thickener that can be incorporated into the compositions of the invention in addition to the crosslinked acrylic copolymer herein described can range from about 0.1 wt. % to about 5 wt. % in one aspect, from about 0.2 wt. % to about 1.5 wt. % in another aspect, and from 0.5 wt. % to about 0.8 wt. % in a further aspect of the invention, based on the total weight of the composition.

The auxiliary anionic thickeners are simultaneously neutralized with alkaline pH adjusting agents that are utilized to neutralize the crosslinked acrylic copolymers of the invention.

Surprisingly, it has been discovered that combinations of powdered polymers conforming to the INCI designation of Carbomer or powdered copolymers conforming to INCI designation Acrylates/C10-30 Alkyl Acrylate Crosspolymer with the crosslinked acrylic copolymer described herein give superior gel and styling properties such as, for example, clarity, yield value, short flow, and viscosity profiles. It has been unexpectedly found that increasing the fixative polymer level in a hair styling composition does not adversely affect gel consistency (e.g., clarity, shear thinning, and yield value is maintained) and viscosity profiles. Consequently, the styling performance of a hair styling composition can be enhanced without deleteriously affecting gel properties and viscosity.

By the term "powder" is meant that the polymer is in solid form (not an emulsion) and passes through a 20 mesh screen (U.S. Standard Mesh). The term powder is defined in Hawley's Condensed Chemical Dictionary, $14^{th}$ Edition, 2001, John Wiley & Sons, Inc., New York, on page 921, which is herein incorporated by reference for the disclosure thereof.

Polymers conforming to the INCI designation Carbomer are homopolymers of (meth)acrylic acid crosslinked with allyl ether of pentaerythritol, an allyl ether of sucrose, or an allyl ether of propylene.

Polymers conforming to the INCI designation Acrylates/C10-30 Alkyl Acrylate Crosspolymer are copolymers of $C_{10}$-$C_{30}$ alkyl acrylates with one or more monomers selected from (meth)acrylic acid, $C_1$-$C_4$ alkyl esters of (meth)acrylic acid, and combinations thereof, crosslinked with an allyl ether of sucrose or an allyl ether of pentaerythritol.

If desired, the viscosity of the hair styling gel and personal care compositions of the invention can be adjusted. The viscosity of the hair styling gels should be effective to provide hair fixative properties to the gels. Where the viscosity of the polymer is too high, the gels and films formed therefrom exhibit unacceptable haziness. Where the viscosity is too low, properties such as stiffness and humidity resistance, gel, and gel aesthetics are adversely affected. Higher molecular weight fixative polymers give gels of higher viscosities, while lower molecular weight fixative polymers give gels with lower viscosities. The viscosity profiles of the polymers in the gels can also be adjusted by controlling the degree of neutralization (DN) of the fixative polymer. Higher DN values result in higher gel viscosities, while lesser degrees of neutralization result in lower gel viscosities. In one aspect of the invention, the DN of the fixative/thickener polymer ranges from about 50% to about 70%. In another aspect of the invention, the DN of the polymer is ≥70%. In still another aspect, for high clarity gels a DN of ≥70% can be utilized. In addition, a salt such as sodium chloride or sodium sulfate can be added to the composition to lower the viscosity to a desired level.

The alkaline neutralizing agents that can be used to neutralize the crosslinked acrylic copolymer fixative/thickeners of the present invention and the optional anionic auxiliary thickeners include inorganic bases, organic bases, and combinations thereof. Examples of inorganic bases include but are not limited to the alkali metal hydroxides (especially lithium, sodium, potassium, magnesium, and ammonium), and alkali metal salts of inorganic acids, such as sodium borate (borax), sodium phosphate, sodium pyrophosphate, and the like; and mixtures thereof. Examples of organic bases include but are not limited to triethanolamine (TEA), diisopropanolamine, triisopropanolamine, aminomethyl propanol (2-Amino-2-methyl-1-propanol), dodecylamine, cocamine, oleamine, morpholine, triamylamine, triethylamine, tetrakis (hydroxypropyl)ethylenediamine, L-arginine, methyl glucamine, isopropylamine, aminomethyl propanol, tromethamine (2-amino 2-hydroxymethyl-1,3-propanediol), and PEG-15 cocamine. Alternatively, other alkaline materials can be used alone or in combination with the above mentioned inorganic and organic bases.

The crosslinked acrylic fixative/thickener polymers of the invention can be formulated solely in water as the solvent, or the diluent system can be a blend of polar organic solvent and water. Typically, the organic solvent will be selected from an alcohol, a ketone, an ether, and mixtures thereof. In one aspect, suitable solvents are low boiling alcohols selected from $C_1$-$C_4$ linear or branched alcohols and denatured alcohols. Exemplary polar solvents include, but are not limited to, ethanol, propanol, isopropanol, butanol, acetone, methyl ethyl ketone, dimethylether, and dimethoxymethane. Another exemplary polar solvent includes methyl acetate and ethyl acetate. Mixtures of the individual solvents disclosed above are also contemplated. In one aspect, the amount of solvent ranges from about 1 wt. % to about 40 wt. %, from about 5 wt. % to about 25 wt. % in another aspect, and from about 6 wt. % to about 10 wt. % in a further aspect of the invention, based on the total wt. of the composition.

The crosslinked acrylic fixative/thickener polymers of the invention can include an optional auxiliary fixative agent. Suitable optional auxiliary hair fixative polymers include natural and synthetic polymers such as, for example, polyacrylates, polyvinyls, polyesters, polyurethanes, polyamides, modified cellulose, starches, and mixtures thereof. These polymers can be nonionic, anionic, cationic and amphoteric in nature and include without limitation one or more of polyoxyethylenated vinyl acetate/crotonic acid copolymers, vinyl acetate crotonic acid copolymers, vinyl methacrylate copolymers, monoalkyl esters of poly(methyl vinyl ether (PVM)/maleic anhydride (MA)), such as, for example, ethyl, butyl and isopropyl esters of PVM/MA copolymer acrylic acid/ethyl acrylate/N-tert-butyl-acrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, vinyl acetate (VA)/crotonates/vinyl neodeanoate copolymer, poly(N-vinyl acetamide), poly(N-vinyl formamide), corn starch modified, sodium polystyrene sulfonate, polyquaterniums such as, for example, Polyquaternium-4, Polyquaternium-5, Polyquaternium-6, Polyquaternium-7, Polyquaternium-10, Polyquaternium-11, Polyquaternium-22, Polyquaternium-24, Polyquaternium-28, Polyquaternium-29, Polyquaternium-32, Polyquaternium-34, Polyquaternium-37, Polyquaternium-39, Polyquaternium-44, Polyquaternium-46, Polyquaternium-47, Polyquaternium-52, Polyquaternium-53, Polyquarternium-55, Polyquaternium-68, Polyquaternium-69, Polyquaternium-87, Laureth-16, polyether-1, VA/acrylates/lauryl methacrylate copolymer, adipic acid/dimethylaminohydroxypropyl diethylene AMP/acrylates copolymer, methacrylol ethyl betaine/acrylates copolymer, acrylamide/sodium acryloyldimethyltaurate/acrylic acid, polyvinylpyrrolidone (PVP), vinyl pyrrolidone (VP)/dimethylaminoethylmethacrylate copolymer, acrylic acid/VP crosspolymer, VP/methacrylamide/vinyl imidazole copolymer, VP/dimethylaminopropylamine (DMAPA) acrylates copolymer, VP/vinylcaprolactam/DMAPA acrylates copolymer, vinyl caprolactam/VP/dimethylaminoethyl methacrylate copolymer, VA/butyl maleate/isobornyl acrylate copolymer, VA/crotonates copolymer, acrylate/acrylamide copolymer, VA/crotonates/vinyl propionate copolymer, VP/vinyl acetate/vinyl propionate terpolymers, VP/vinyl acetate copolymer, VP/acrylates copolymer, VA/crotonic acid/vinyl proprionate, acrylates/acrylamide, acrylates/octylacrylamide, acrylates/hydroxyacrylates copolymer, acrylates/hydroxyesteracrylates copolymer, acrylates/stereth-20 methacrylate copolymer, tert-butyl acrylate/acrylic acid copolymer, diglycol/cyclohexanedimethanol/isophthalates/sulfoisophthalates copolymer, VA/alkylmaleate half ester/N-substituted acrylamide terpolymers, vinyl caprolactam/VP/methacryloamidopropyl trimethylammonium chloride terpolymer, methacrylates/acrylates copolymer/amine salt, polyvinylcaprolactam, hydroxypropyl guar, poly(methacrylic acid/acrylamidomethyl propane sulfonic acid (AMPSA), ethylenecarboxamide (EC)/AMPSA/methacrylic acid (MAA), poylurethane/acrylate copolymers and hydroxypropyl trimmonium chloride guar, acrylates crosspolymer, AMP-acrylates/allyl methacrylate copolymer, polyacrylate-14, polyacrylate-2 crosspolymer, acrylates/lauryl acrylate/stearyl acrylate/ethylamine oxide methacrylate copolymer, methacryloyl ethyl betaines/methacrylates copolymer, polyurethane/acrylates copolymer, pyrrolidone carboxylic acid salt of chitosan, chitosan glycolate, cationic polygalactomannans, such as, for example, quaternized derivatives of guar, such as, for example, guar hydroxypropyl trimmonium chloride, cassia hydroxypropyl trimmonium chloride and hydroxypropyl guar hydroxypropyl trimmonium chloride. Many of the foregoing polymers are referred to by their INCI nomenclature set forth in the International Cosmetic Ingredient Dictionary published by the Cosmetic, Toiletry, and Fragrance Association, Washington D.C. Other suitable auxiliary fixative polymers are disclosed in U.S. Pat. No. 7,205,271, the disclosure of which is herein incorporated by reference.

The auxiliary fixative polymer typically comprises about 0.01 wt. % to about 8 wt. % in one aspect, from about 0.1 wt. % to about 5 wt. % in another aspect, and about 0.2 wt. % to about 3 wt. % in a further aspect of the total weight of the hair styling composition.

In one embodiment of the invention, the fixative/thickener/film former polymers of the invention can be formulated in combination with derivatized and non-derivatized hydrocolloids obtained from natural sources such as, for example, polysaccharides obtained from tree, shrub, and fruit exudates, such as gum arabic, gum gahatti, and gum tragacanth, and pectin; seaweed extracts, such as alginates and carrageenans; algae extracts, such as agar; microorganism produced polysaccharides, such as xanthan, gellan, and wellan gums; cellulose ethers, such as ethylhexylethylcellulose (EHEC), hydroxybutylmethylcellulose (HBMC), hydroxyethylmethylcellulose (NEMC), hydroxypropylmethylcellulose (HPMC), methyl cellulose (MC), carboxymethylcellulose (CMC), hydroxyethylcellulose (HEC), hydroxypropylcellulose (HPC) and cetyl hydroxyethylcellulose; polygalactomannan gums selected from fenugreek, cassia, locust bean, tara and guar; and mixtures thereof.

By derivatized hydrocolloid is meant that the above mentioned hydrocolloids can be derivatized with a functionalization agent reactive with a functional group, e.g., a hydroxyl group, contained on the hydrocolloid backbone. For example, derivatives of the cellulose ethers containing quaternary ammonium groups can be made by reacting a cellulose ether, e.g., hydroxyethylcellulose, with an epoxide containing a trialkyl ammonium salt group, e.g., glycidyltrimethylammonium chloride, to give the corresponding quaternary substituted cellulose.

Derivatized hydrocolloids can also be made by quaternizing a polygalactomannan such as locust bean gum, cassia or guar with a quaternizing agent. Quaternized polygalactomannans can be made by reacting guar gum with a haloalkyl substituted quaternary ammonium compound, e.g., 4-chloro-2-butenyl trimethylammonium chloride. A process for producing derivatized polygalactomannan gums is described in U.S. Pat. No. 4,031,307.

When the above mentioned hydrocolloids are formulated into the compositions of the present invention, the weight ratio of crosslinked anionic copolymer fixative to hydrocolloid(s) range from about 1:10 to about 10:1 in one aspect, from about 2:8 to about 8:2 in another aspect, from about 2.5:7.5 to about 7.5:2.5 in a further aspect, from about 1:5 to about 5:1 in another aspect, and from about 1:2 to about 2:1 in a still further aspect.

In one aspect of the invention, the viscosity of a hair styling gel composition or personal care composition comprising a crosslinked acrylic fixative/thickener polymer of the invention with and without the optional Carbomers or powdered Acrylates/C10-30 Alkyl Acrylate copolymers in water is from about 8,000 to about 80,000 mPa·s in one aspect, from about 10,000 to about 60,000 mPa·s in another aspect, from about 12,000 to about 40,000 mPa·s in a further aspect, and from about 15,000 to about 30,000 mPa·s in a still further aspect, as measured on a Brookfield viscometer with a No. 5 or 6 spindle at 20 rpm, and at ambient room temperature.

Optional conventional additives also can be incorporated into the hair styling compositions and personal care compositions of the invention to provide certain modifying and aesthetic properties. The identity of the optional additives is not limited so long as the optional additives do not adversely affect the efficacy or aesthetics of the hair styling and personal care compositions. Such optional additives are well known to those skilled in the art. Included among these additives are conditioners, moisturizers, emollients, plasticizers, natural and synthetic waxes, emulsifiers, fragrances and fragrance solubilizers, vitamins, proteins, botanicals, pigments and colorants, sunscreen agents, buffers, pH adjusting agents, sheen enhancing agents, electrolytes, chelating agents, insoluble components, preservatives, and combinations thereof. These additives are present in amounts effective to accomplish their function, and generally will each comprise from about 0.01 wt. % to about 20 wt. %, in one aspect, from about 0.1 wt. % to about 10 wt. % in another aspect, and from about 0.5 wt. % to about 3 wt. % in a further aspect, based on the total weight of the composition. The precise amount of each additive or adjuvant to employ in a desired composition can be easily determined by one of ordinary skill in the field according to the nature and function of the ingredient. Those skilled in the hair styling and personal care arts recognize that some ingredients described herein are multifunctional and, hence, can serve more than one purpose in the formulation, as long as the purpose and properties of the hair setting composition performs its intended function. While a particular ingredient may be exclusively listed herein under a particular heading for a disclosed purpose, it will be recognized that it does not necessarily mean that the listed additive serves only the listed function. An extensive listing of cosmetic ingredients and their functions appears in the INCI Dictionary, generally, and in Vol. 2, Section 4 of the Seventh Edition, both of which are incorporated herein by reference.

Conditioners

Any conditioning agent suitable for use in hair styling and skin care compositions can be used in the compositions of the present invention. Conditioning agents can be selected from mineral oils, vegetable oils, fluorinated oils, vegetable oils, natural and synthetic waxes, fatty acids and fatty acid derivatives, proteins, hydrolyzed proteins, silicones (e.g. polyalkylsiloxanes, polyarylsiloxanes, polyalkylarylsiloxanes, cyclomethicones, dimethicones, dimethicone copolyols, amodimethicones, panthenol, and the like), and cationic polymers and compounds. The silicones can be in the form of fluids, oils, emulsions (micro- or macro-emulsions), gums, or resins, and can be volatile or non-volatile, and water soluble or water insoluble.

In one aspect, cationic conditioning agents can be employed in the compositions disclosed herein. Those of ordinary skill in the art will recognize that many of these cationic conditioning agents serve multiple functions. Typically, these agents are useful as conditioners (e.g., hair and skin), fixatives, antistatic agents, and as antimicrobial agents. Cationic polymers can be synthetically derived or obtained by modifying natural polymers such as the cationically modified polysaccharides and polygalactomannans.

Exemplary conditioning agents include, but are not limited to, homopolymers and copolymers derived from free radically polymerizable acrylic or methacrylic ester or amide monomers. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Exemplary polymers include copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT™ by International Specialty Products Inc., Wayne, N.J.; the dimethyl amino ethyl methacrylate/vinyl caprolactam/vinyl pyrrolidone terpolymers, such as the product sold under the trade name GAFFIX™ VC 713 by International Specialty Products Inc.; the vinyl pyrrolidone/methacrylamidopropyl dimethylamine copolymer, available from International Specialty Products Inc.; and the vinyl pyrrolidone/quaternized dimethyl amino propyl methacrylamide copolymers such as the product sold under the trade name GAFQUAT™ HS100 by International Specialty Products, Inc; and the polymeric quaternary ammonium salt formed by the reaction of diethyl sulfate and a copolymer of vinyl pyrrolidone and dimethyl aminoethylmethacrylate such as the product sold under the trade name GAFQUAT™ 755 by International Specialty Products, Inc.

Cationic agents can also be selected from the quaternary copolymers of vinyl pyrrolidone and vinyl imidazole such as the products sold under the trade name Luviquat® (product designations FC 370, FC 550, Excellence, Style, and Ultracare); the quaternary terpolymers of vinyl pyrrolidone, acrylamide and vinyl imidazole such as the products sold under the trade name Luviquat® (product designation Supreme), the quaternary terpolymers of vinyl caprolactam, vinyl pyrrolidone and vinyl imidazole such as the products sold under the trade name Luviquat® (product designation Hold), the quaternary terpolymers of vinyl pyrrolidone, vinyl imidazole, and diallyldimethyl ammonium chloride such as the products sold under the trade name Luviquat® Sensation by BASF. Other cationic polymer agents that can be used in the compositions of the invention include polyalkyleneimines such as polyethyleneimines, polymers containing vinyl pyridine or vinyl pyridinium units, condensates of polyamines and epichlorhydrins, quaternary polysaccharides, quaternary polyurethanes, quaternary silicones, and quaternary derivatives of chitin.

Other non-limiting examples of quaternary ammonium compounds (monomeric and polymeric) useful as cationic agents in the present invention include acetamidopropyl trimonium chloride, behenamidopropyl dimethylamine, behenamidopropyl ethyldimonium ethosulfate, behentrimonium chloride, behentrimonium methosulfate, cetethyl morpholinium ethosulfate, cetrimonium chloride, cocoamidopropyl ethyldimonium ethosulfate, dicetyldimonium chloride, pyridoxine HCl, dimethicone hydroxypropyl trimonium chloride, hydroxyethyl behenamidopropyl dimonium chloride, Quaternium-22, Quaternium-26, Quaternium-27, Quaternium-52, Quaternium-53, Quaternium-63, Quaternium-70, Quaternium-72, Quaternium-76, hydrolyzed collagen, PEG-2-cocomonium chloride, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, Polyquaternium-1, Polyquaternium-4, Polyquaternium-5, Polyquaternium-6, Polyquaternium-7, Polyquaternium-10, Polyquaternium-11, Polyquaternium-15, Polyquarternium-16, Polyquaternium-22, Polyquaternium-24, Polyquaternium-28, Polyquaternium-29, Polyquaternium-32, Polyquaternium-33, Polyquaternium-35, Polyquaternium-37, Polyquaternium-39, Polyquaternium-44, Polyquaternium-46, Polyquaternium-47, Polyquaternium-52, Polyquaternium-53, Polyquarternium-55, Polyquaternium-59, Polyquaternium-61, Polyquaternium-64, Polyquaternium-65, Polyquaternium-67, Polyquaternium-69, Polyquaternium-70, Polyquaternium-71, Polyquaternium-72, Polyquaternium-73, Polyquaternium-74, Polyquaternium-76, Polyquaternium-77, Polyquaternium-78, Polyquaternium-79, Polyquaternium-80, Polyquaternium-81, Polyquaternium-82, Polyquaternium-84, Polyquaternium-85, Polyquaternium-87, Polyquaternium-89, Polyquaternium-90, Polyquaternium-91, Polyquaternium-92, Polyquaternium-94, Polyquaternium-95, Polyquaternium-96, PEG-2-cocomonium chloride; and mixtures thereof.

The monomeric quaternary ammonium compounds include, for example, alkylbenzyldimethyl ammonium salts, betaines, heterocyclic ammonium salts, and tetraalkylammonium salts. Long-chain (fatty) alkylbenzyldimethyl ammonium salts are utilized as conditioners and as antistatic agents.

Non-limiting examples of alkylbenzyldimethylammonium salts include, but are not limited to, stearalkonium chloride, benzalkonium chloride, Quaternium-63, olealkonium chloride, didecyldimonium chloride, and the like. The betaine compounds (amphoteric) include the alkylamidopropyl betaines and the alkylamidopropyl hydroxysultaines. Non-limiting examples of alkyl betaine compounds include oleyl betaine, coco-betaine, cocoamidopropyl betaine, coco-hydroxy sultaine, coco/oleamidopropyl betaine, coco-sultaine, cocoamidopropylhydroxy sultaine, and sodium lauramidopropyl hydroxyphostaine.

The heterocyclic ammonium salts include the alkylethyl morpholinium ethosulfates, isostearyl ethylimidonium ethosulfate, and the alkylpyridinium chlorides. Non-limiting examples of heterocyclic ammonium salts include, but are not limited to, cetylpyridinium chloride, isostearylethylimidonium ethosulfate, and the like.

Non-limiting examples of tetraalkylammonium salts include cocamidopropyl ethyldimonium ethosulfate, hydroxyethyl cetyldimonium chloride, Quaternium-18, and cocodimonium hyroxypropyl hydrolyzed protein, such as hair keratin, and the like.

A number of quaternary ammonium compounds are used as antistatic agents. They include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride.

In addition, other types of long chain (e.g., natural oil and fatty acid-derived) alkylated quaternary ammonium compounds are suitable conditioning agents. In one aspect, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, and palmityl groups.

The foregoing monomeric and polymeric quaternary ammonium salt compounds can have any anionic group as a counter-ion, for example, chloride, bromide, methosulfate (i.e., methylsulfate), acetate, formate, sulfate, nitrate, and the like.

As described above, many of the disclosed ingredients described herein are multifunctional and, hence, can serve more than one purpose in the formulations of the invention. Thus, as is apparent to those of ordinary skill in the art, many of the ingredients described herein and below (e.g., moisturizers, emollients, emulsifiers, plasticizers, vitamins, and the like) can serve as a conditioning agent herein so long as they function to improve the cosmetic and cosmeceutical properties of the hair.

In one aspect, the cationic conditioning agent(s) can be employed in amounts ranging from about 0.005 wt. % to 5 wt. %, from about 0.01 wt. % to about 3 wt. % in another aspect, and from about 0.05 wt. % to about 1 wt. % in a further aspect, based on the total weight of the composition, but is not limited thereto.

Moisturizers

Another ingredient which may be formulated with the hair styling and personal care compositions of the present invention is a moisturizer. As used herein, a "moisturizer" is an ingredient which promotes the retention of water to the surface area of the human body, including hair and scalp. Moisturizers that may used in accordance with the present invention include, without limitation, polyhydroxy alcohols, including butylene glycol, hexylene glycol, propylene glycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example, aloe vera gel; sugars and starches; sugar and starch derivatives, for example alkoxylated glucose; hyaluronic acid; lactamide monoethanolamine; acetamide monoethanolamine; glycolic acid; alpha and beta hydroxy acids (e.g. lactic, glycolic and salicylic acid); glycerine; panthenol; patothenic acid, urea; vaseline; natural oils; oils and waxes (see the emollients section herein) and mixtures thereof. Moisturizers are generally recognized in the art of personal care, hair care, and skin care and in principle any moisturizer may be formulated into the compositions of the present invention.

The moisturizer will generally comprise from about 0.1 wt. % to about 15 wt. % in one aspect, from about 1 wt. % to about 10 wt. % in another aspect, and from 3 wt. % to about 8 wt. % in a further aspect, based on the total weight of the composition. Although the ingredients mentioned herein are generally defined as moisturizers, they may also possess other properties such as emolliency or other conditioning properties.

Emollients

Suitable emollients and lubricants include but are not limited to compositions selected from silicone fluids (e.g., volatile silicone oils and non-volatile silicone oils); mineral oils; petrolatums, hydrocarbon oils, liquid polyolefin oils, fluorinated and perfluorinated oils, natural oils (e.g., vegetable oils; fish oils), glycerin and glyceride derivatives, fatty alcohols, alkoxylated fatty alcohols, fatty acids; fatty acid and fatty alcohol esters, alkoxylated fatty acid esters, benzoate esters, Guerbet esters, alkyl ether derivatives of polyethylene glycols, such as, for example, methoxypolyethylene glycol (MPEG); and polyalkylene glycols, lanolin and lanolin derivatives, natural and synthetic waxes; and the like.

The volatile silicones include cyclic and linear polydimethylsiloxanes, and the like. "Volatile" means that the silicone has a measurable vapor pressure, or a vapor pressure of at least 2 mm of Hg at 20° C. The linear volatile silicones are silicone fluids, as described above, having viscosities of not more than about 25 mPa·s. A description of cyclic and linear volatile silicones is found in Todd and Byers, "Volatile Silicone Fluids for Cosmetics", Cosmetics and Toiletries, Vol. 91(1), pp. 27-32 (1976), and in Kasprzak, "Volatile Silicones", Soap/Cosmetics/Chemical Specialties, pp. 40-43 (December 1986), each incorporated herein by reference.

The volatile cyclic polysiloxanes (cyclomethicones) contain about 3 to about 7 silicon atoms, alternating with oxygen atoms, in a cyclic ring structure represented as follows:

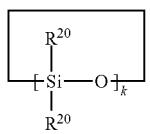

wherein $R^{20}$ is an aliphatic group, independently selected from alkyl, alkenyl, and aryl, and k ranges from about 3 to about 7. In one aspect, $R^{20}$ is independently selected from a methyl and phenyl. However, each $R^{20}$ substituent and the number of repeating units, k, in the formula are selected so that the compound is volatile. Typically, the $R^{20}$ substituent is substituted with two alkyl groups (e.g., methyl).

The volatile linear polydimethylsiloxanes can be represented by the formula:

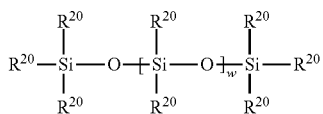

wherein $R^{20}$ is defined as above, and w ranges from 1 to about 8,000 in one aspect, from about 1 to 1000 in another aspect, from 1 to about 500 in a further aspect, and from about 1 to about 250 in a still further aspect. In one aspect, $R^{20}$ is independently selected from a methyl and phenyl. However, each $R^{20}$ substituent and the number of repeating units, w, in the formula are selected so that the compound is volatile.

Exemplary volatile cyclomethicones are D4 cyclomethicone (octamethylcyclotetrasiloxane), D5 cyclomethicone (decamethylcyclopentasiloxane), D6 cyclomethicone (dodecamethylcyclohexasiloxane), and blends thereof (e.g., D4/D5 and D5/D6). Volatile cyclomethicones and cyclomethicone blends are commercially available from Momentive Performance Materials Inc. as SF1202, SF 1214, SF1256, and SF1258, Dow Corning, Midland, Mich. under the Xiameter® cyclomethicone fluid product designations PMX-0244, PMX-245, PMX-246, PMX-345, and Dow Corning® 1401 fluid. Blends of volatile cyclomethicones and volatile linear dimethicones are also contemplated within the scope of the invention.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning as Xiameter® PMX-200 silicone fluids (e.g., product designations 0.65 CS, 1 CS, 1.5 CS, and 2 CS) and Xiameter® PMX 2-1184 silicone fluid.

Silicone oils include polyalkyl, polyaryl siloxanes, or polyalkylaryl siloxanes which conform to the following formula:

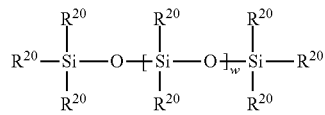

wherein $R^{20}$ is an aliphatic group, independently selected from alkyl, alkenyl, and aryl, $R^{20}$ can be substituted or unsubstituted, and w is an integer from 1 to about 8,000. Suitable unsubstituted $R^{20}$ groups for use in the present invention include, but are not limited to alkoxy, aryloxy, alkaryl, arylalkyl, arylalkenyl, alkamino, and ether-substituted, hydroxyl-substituted, and halogen-substituted aliphatic and aryl groups. Suitable $R^{20}$ groups also include amines, cationic amines and quaternary ammonium groups (e.g., amodimethicone).

In one aspect of the invention, exemplary $R^{20}$ alkyl and alkenyl substituents include $C_1$-$C_5$ alkyl and $C_1$-$C_5$ alkenyl groups. In another aspect, $R^{20}$ is methyl. The aliphatic portions of other alkyl- and alkenyl-containing groups (such as alkoxy, alkaryl, and alkamino) can be straight or branched chains, and contain from $C_1$-$C_5$ in one aspect, from $C_1$-$C_4$ in another aspect, and from $C_1$-$C_2$ in a further aspect. As discussed above, the $R^{20}$ substituents can also contain amino functionalities (e.g., alkamino groups), which can be primary, secondary or tertiary amines or quaternary ammonium. These include mono-, di- and tri-alkylamino and alkoxyamino groups, wherein the aliphatic portion chain length is as described above. Exemplary aryl groups in the foregoing embodiments include phenyl and benzyl.

Exemplary siloxanes are polydimethyl siloxane, polydiethylsiloxane, and polymethylphenylsiloxane. These siloxanes are available, for example, from Momentive Performance Materials in their Viscasil R and SF 96 series, and from Dow Corning marketed under the Dow Corning 200 series. Exemplary polyalkylaryl siloxane fluids that may be used, include, for example, polymethylphenylsiloxanes. These siloxanes are available, for example, from Momentive Performance Materials as SF 1075 methyl phenyl fluid or from Dow Corning as 556 Cosmetic Grade Fluid, or from Wacker Chemical Corporation, Adrian, Mich., under the trade name Wacker-Belsil® PDM series of phenyl modified silicones (e.g., PDM 20, PDM 350 and PDM 1000).

Mineral oils and petrolatums include cosmetic, USP and NF grades and are commercially available from Penreco under the Drakeol® and Penreco® trade names. Mineral oil includes hexadecane and paraffin oil.

Hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils typically contain about 12 to 19 carbon atoms. Branched chain hydrocarbon oils, including hydrocarbon polymers, typically will contain more than 19 carbon atoms. Specific non-limiting examples of these hydrocarbon oils include paraffin oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-octamethyl-10-methylundecane and 2,2,4,4,6,6-hexamethyl-8-methylnonane, available from Permethyl Corporation. Hydrocarbon polymers such as polybutene and polydecene.

Liquid polyolefin oils can be used in the compositions of the present invention. The liquid polyolefin agents are typically poly-α-olefins that have been hydrogenated. Polyolefins for use herein can be prepared by the polymerization of $C_4$ to about $C_{14}$ olefinic monomers. Non-limiting examples of olefinic monomers for use in preparing the polyolefin liquids herein include ethylene, propylene, 1-butene, 1-pentene, 1-hexene, 1-octene, 1-decene, 1-dodecene, 1-tetradecene, and 1-hexadecene, branched isomers such as isobutylene, 4-methyl-1-pentene, and mixtures thereof. In one aspect, a suitable hydrogenated polyolefin is the copolymer of isobutylene and butene. A commercially available material of this type is Panalane® L-14E (INCI Name: Hydrogenated Polyisobutene) marketed by Lipo Chemicals Inc, Patterson, N.J.

Fluorinated and perfluorinated oils contemplated within the scope of the present invention include perfluoropolyethers described in European Patent No. EP 0 486 135 and the fluorohydrocarbon compounds described in International Patent Application Publication No. WO 93/11103. The fluorinated oils may also be fluorocarbons such as fluoramines, e.g., perfluorotributylamine, fluoridated hydrocarbons, such as perfluorodecahydronaphthalene, fluoroesters, and fluoroethers.

Natural oils that are useful in the practice of this invention include, but are not limited to, peanut, sesame, avocado, coconut, cocoa butter, canola, babassu, almond, corn, grape seed, cottonseed, sesame seed, walnut, castor, olive, jojoba, palm, palm kernel, soybean, wheat germ, linseed, safflower, shea nut, sunflower seed, eucalyptus, lavender, vetiver, litsea, cubeba, lemon, sandalwood, rosemary, chamomile, savory, nutmeg, cinnamon, hyssop, caraway, orange, geranium, cade, and bergamot oils, fish oils, as well as glycerides (mono- diand triglycerides) derived from plant oils, vegetable oils, and animal fats (e.g., tallow and lard); and mixtures thereof. The hydrogenated derivatives of natural oils also are contemplated.

Suitable glycerides (mono-, di-, and triglycerides) can be derived through the esterification of glycerol, a monoglyceride, or a diglyceride with a fatty acid(s) by techniques well known in the art, or by glycerolysis of animal fats and vegetable oils in the presence of a base at elevated temperature and under an inert atmosphere (See RSC Green Chemistry Book Series, The Royal Society of Chemistry, *The Future of Glycerol: New Uses Of A Versatile Material*, Chapter 7, Mario Pagliaro and Michele Rossi, © 2008). Fatty acids suitable for use in the esterification reaction include saturated and unsaturated $C_8$-$C_{30}$ fatty acids.

The fatty alcohols suitable for use in the compositions of the invention include, but are not limited to, the saturated and unsaturated $C_8$-$C_{30}$ fatty alcohols. Exemplary fatty alcohols include capryl alcohol, pelargonic alcohol, capric alcohol, decyl alcohol, undecyl alcohol, lauryl alcohol, myristyl alcohol, cetyl alcohol, isocetyl alcohol, stearyl alcohol, isostearyl alcohol, cetearyl alcohol, palmitoleyl alcohol, elaidyl alcohol, sterol, oleyl alcohol, linoleyl alcohol, elaidolinoleyl alcohol, linolenyl alcohol, ricinoleyl alcohol, arachidyl alcohol, icocenyl alcohol, behenyl alcohol, erucyl alcohol, lignoceryl alcohol, ceryl alcohol, montanyl alcohol, myricyl alcohol, and mixtures thereof. Fatty alcohols are widely available and can be obtained through the hydrogenation of esterified vegetable and animal oils and fats.

Alkoxylated fatty alcohol compounds are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the invention, the ethoxylated fatty alcohols can be represented by the formula R'''—(OCH$_2$CH$_2$)$_{n''}$—OH, wherein R''' represents the aliphatic residue of the parent fatty alcohol and n'' represents the number of ethylene oxide units. In another aspect of the invention, R''' is derived from a fatty alcohol containing 8 to 30 carbon atoms. In one aspect, n'' is an integer ranging from 2 to 50, 3 to 25 in another aspect, and 3 to 10 in a further aspect. In a still further aspect, R''' is derived from a fatty alcohol set forth immediately in the paragraph above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the invention. The ethylene oxide and propylene oxide units of the ethoxylated/propoxylated fatty alcohols can be arranged in random or in blocky order.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

Additional examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, 09-11 Pareth 3-8, 011-15 Pareth 5-40, 011-21 Pareth 3-10, 012-13 Pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 $C_{9-15}$ Pareth-6, PPG-6 C911

Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Suitable fatty acids include saturated and unsaturated $C_8$ to $C_{30}$ fatty acids. Exemplary fatty acids include, but are not limited to, caprylic acid, capric acid, lauric acid, myristic acid, palmitic acid, palmitoleic acid, stearic acid, oleic acid, ricinoleic acid, vaccenic acid, linoleic acid, α-linolenic acid, γ-linolenic acid, arachidic acid, gadoleic acid, arachidonic acid, EPA (5,8,11,14,17-eicosapentaenoic acid), behenic acid, erucic acid, DHA (4,7,10,13,16,19-docosahexaenoic acid), lignoceric acid, and mixtures thereof.

Fatty acids can be esterified by alcohols in the presence of a suitable acid catalyst to give a desired fatty acid ester. In one aspect, any of the saturated and unsaturated $C_8$ to $C_{30}$ fatty acids disclosed above can be esterified by a saturated or unsaturated $C_1$ to $C_{22}$ alcohol to give the respective fatty acid ester. In another aspect, longer chain fatty acid esters can be derived from the esterification of the above mentioned fatty acids by a saturated or unsaturated $C_8$ to $C_{30}$ fatty alcohol and can be represented by the formula: R"C(O)OR" wherein R" independently represents a saturated and unsaturated, linear and branched alkyl group containing 1 to 24 carbon atoms. Suitable fatty alcohols include the fatty alcohols that are disclosed above.

Exemplary fatty acid esters include, but are not limited to, methyl laurate, hexyl laurate, isohexyl laurate, decyl oleate, methyl cocoate, isopropyl stearate, isopropyl isostearate, butyl stearate, decyl stearate, octyl stearate, cetyl stearate, stearyl stearate, oleyl stearate, myristyl myristate, octyldodecyl stearoyl stearate, octylhydroxystearate, isopropyl myristate, oleyl myristate, isopropyl palmitate, ethyl hexyl palmitate, cetyl palmitate, decyl oleate, isodecyl oleate, oleyl oleate, isodecyl neopentanoate, diisopropyl sebacate, isostearyl lactate, lauryl lactate, cetearyl octanoate, and mixtures thereof.

Still other fatty acid esters suitable for use in the fixative compositions of the present invention are mono-, di- and tri-alkyl and alkenyl esters of carboxylic acids, such as esters of $C_2$ to $C_8$ monocarboxylic acids, $C_4$ to $C_{10}$ dicarboxylic acids, and $C_6$ to $C_{10}$ tricarboxylic acids (e.g., $C_1$ to $C_{22}$ esters of acetic acid, lactic acid, succinic acid, glutaric acid, adipic acid, citric acid, trimelletic acid, trimesic acid, and 1,3,5-pentane tricarboxylic acid). Specific non-limiting examples of mono-, di- and tri-alkyl and alkenyl esters of carboxylic acids include lauryl acetate, cetyl propionate, lauryl lactate, myristyl lactate, cetyl lactate, diisopropyl adipate, dihexyldecyl adipate, dioleyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono- and di-fatty acid esters, diethylene glycol mono- and di-fatty acid esters, polyethylene glycol mono- and di-fatty acid esters, propylene glycol mono- and di-fatty acid esters, polypropylene glycol mono- and di-fatty acid esters, and sorbitol mono- and di-fatty esters, wherein the acyl portion of the fatty acid ester is derived from a saturated or unsaturated $C_8$ to $C_{22}$ fatty acid. These esters can be optionally ethoxylated. Representative polyhydric alcohol fatty acid esters include, but are not limited to, polypropylene glycol monooleate, polypropylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Other polyhydric alcohol esters include the partial esters of polyglycerols. These esters contain 2 to 10 glycerol units and are esterified with 1 to 4 saturated or unsaturated, linear or branched, optionally hydroxylated $C_8$ to $C_{30}$ fatty acid residues. Representative partial esters of polyglycerols include, but are not limited to, diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

Suitable benzoate esters are obtained by the reaction of benzoic acid with a fatty alcohol such as those described above. In one aspect, the fatty alcohol utilized in the esterification reaction is a $C_{12}$-$C_{15}$ fatty alcohol. Such esters are described in U.S. Pat. No. 4,275,222 which is incorporated herein by reference.

Guerbet esters are also suitable in the fixative compositions of the invention. Guerbet esters can be formed from the esterification of a mono- or polyfunctional carboxylic acid by a Guerbet alcohol. Alternatively, the ester can be formed by reacting a Guerbet acid with a mono- or polyfunctional alcohol. For a review of Guerbet chemistry, see O'Lenick, A. J., Jr. 2001. Guerbet chemistry. *Journal of Surfactants and Detergents* 4: 311-315. Guerbet esters are commercially available from Lubrizol Advanced Materials, Inc. under product designations G-20, G-36, G-38, and G-66.

Lanolin and lanolin derivatives are selected from lanolin, lanolin wax, lanolin oil, lanolin alcohols, lanolin fatty acids, esters of lanolin fatty acids such as the isopropyl esters of lanolin fatty acid (e.g., isopropyl lanolates), alkoxylated lanolin (ethoxylated, propoxylated, and combinations thereof), acetylated lanolin alcohols; and combinations thereof. Lanolin and lanolin derivatives are commercially available from Lubrizol Advanced Materials, Inc. under the trade names Lanolin LP 108 USP, Lanolin USP AAA, Acetulan™, Ceralan™, Lanocerin™, Lanogel™ (product designations 21 and 41), Lanogene™, Modulan™, Ohlan™, Solulan™ (product designations 16, 75, L-575, 98, and C-24), and Vilvanolin™ (product designations C, CAB, L-101, and P).

The emollient can be used alone or in combination with one or more emollients of the present invention. The emollient(s) can be utilized in an amount ranging from about 0.5 wt. % to about 30 wt. % in one aspect, from about 0.1 wt. % to about 25 wt. % in another aspect, and from about 5 wt. % to about 20 wt. % in a further aspect, based on the total weight of the composition. Although the ingredients mentioned herein are generally defined as emollients, they may also possess other properties such as moisturizing or other conditioning properties.

Plasticizers

One or more plasticizers can be added to the compositions of the present invention. A plasticizer is any material that will contribute to making the hair styling composition or film former less brittle and more flexible when applied to the hair, skin and nails. The plasticizers that can be used in the composition include, for example, dimethicone copolyol(s), polyols, polycarboxylic acids, polyesters, phthalate esters, benzoate esters, ethyoxylated lanolin alcohols; and mixtures thereof.

Exemplary dimethicone copolyols include, but are not limited to, PEG-1 Dimethicone, PEG-7 Dimethicone, PEG-8 Dimethicone, PEG-12 Dimethicone, PEG-14 Dimethicone, PEG-33 Dimethicone, PEG/PPG-15/15 Dimethicone, PEG/PPG-18/18 Dimethicone, PPG-12 Dimethicone; and mixtures thereof. Silsense™ dimethicone copolyols, such as Silsense Copolyol-1 and Silsense Copolyol-7, available from Lubrizol Advanced Materials, Inc. are examples of commercially available dimethicone copolyols.

Exemplary polyols include, but are not limited to, glycerin, glycols containing 2 to 5 carbon atoms (e.g. ethylene glycol, propylene glycol, butylene glycol, neopentyl glycol), polyalkylene glycols (e.g., polyethylene and polypropylene glycols containing 2 to 100 repeating units), sugar alcohols such as sorbitol, manitol, maltitol, lactitol, mono-,di- and oligosaccharides such as fructose, glucose, sucrose, maltose, lactose, and combinations thereof.

Exemplary polycarboxylic acids include, but are not limited to, citric acid, maleic acid, succinic acid, polymaleic acid; and mixtures thereof.

Exemplary polyesters include, but are not limited to, glycerol triacetate, acetylated-monoglyceride, triethyl citrate, tributyl citrate, acetyl triethyl citrate, acetyl tributyl citrate, diethylhexyl adipate, heptyl nonyl adipate, diisodecyl adipate, dicapryl adipate, dimethyl azelate, 2,2,4-trimethyl-1,3-pentanediol diisobutyrate, methyl (or ethyl, or butyl)phthalyl ethyl glycolate, dibutyl fumarate, 2,2,4-trimethyl-1,3-pentanediol diisobutyrate, di-n-butyl maleate, tricapryl trimellitate, heptyl nonyl trimellitate, triisodecyl trimellitate, triisononyl trimellitate, dimethyl sebacate, diethyl succinate, the butyl phenylmethyl ester of 1,2-benzenedicarboxylic acid; and mixtures thereof.

Exemplary phthalate esters include, but are not limited to, dimethyl phthalate, diethyl phthalate, dibutyl phthalate, diisobutyl phthalate, di-2-ethylhexyl phthalate, octyl decyl phthalate, diisodecyl phthalate, heptyl nonyl phthalate, diundecyl phthalate, ditridecyl phthalate, dicyclohexyl phthalate, diphenyl phthalate, butyl benzyl phthalates such as the n-butylbenzyl ester of o-phthalic acid, isodecyl benzyl phthalate, alkyl ($C_7$/$C_9$) benzyl phthalate, dimethoxyethyl phthalate, 7-(2,6,6,8-tetramethyl-4-oxa-3-oxo-nonyl)benzyl phthalate; and mixtures thereof.

Exemplary benzoate esters include, but are not limited to, diethylene glycol dibenzoate and dipropylene glycol dibenzoate (such as the K-Flex® esters from Lubrizol Advanced Materials, Inc.), polyethylene glycol dibenzoate, 2,2,4-trimethyl-1,3-pentanediol monoisobutyrate benzoate; and mixtures thereof.

Other examples of plasticizers include, but are not limited to, the mineral oils, vegetable oils, triglycerides, lanolins and their derivatives, unsaturated fatty acids and their derivatives disclosed above, lactates (including but not limited to sodium, ammonium, and potassium salts), Sorbeth-30; urea, sodium pyrrolidone carboxylic acid (PCA); liposomes, serine, chitosan PCA, sodium hyaluronate, hyaluronic acid, soluble collagen, protein, modified protein, monosodium L-glutamate, lecithins and phospholipids and their derivatives; alpha and beta hydroxy acids such as glycolic acid, lactic acid, citric acid, maleic acid and salicylic acid; polysaccharides and their derivatives, and polyquaterniums, amino acids such as glutamic acid, aspartic acid, and lysine; and mixtures thereof.

Plasticizers will be present in a plasticizing effective amount. In one aspect, the plasticizer can be present in the formulation in an amount from about 0.05 wt. % to about 10 wt. %, from about 0.10 wt. % to about 5 wt. % in another aspect, and from about 0.5 wt. % to about 3 wt. % in a further aspect, based upon total weight of the hair styling composition.

Natural and Synthetic Waxes

The natural and synthetic wax agents that can suitably be employed in the compositions of the invention, include, but are not limited to, carnauba wax, hydrolyzed carnauba wax, carnauba acid wax, ethoxylated carnauba wax (e.g., PEG-12 carnauba wax), candelila wax, hydrolyzed candelilla wax, hydrogenated castor wax, bayberry wax, alfa wax, paraffin wax, ozokerite wax, olive wax, ouricury wax, palm kernel wax, rice wax, hydrogenated jojoba wax, bees wax, modified bees wax, e.g., oxidized beeswax, ethoxylated beeswax (e.g., PEG-6 beeswax, PEG-8 beeswax, PEG-12 beeswax, PEG-20 beeswax), dimethicone copolyol beeswax esters and dimethiconol beeswax ester (e.g., Bis-Hydroxyethoxypropyl Dimethicone Beeswax Esters, Dimethicone PEG-8 Beeswax, and Dimethiconol Beeswax available from Lubrizol Advanced Materials, Inc. under the Ultrabee® trademark), cerabellina wax, marine waxes, lanolin and derivatives thereof, and polyolefin waxes, e.g., polyethylene wax; and mixtures thereof. The amount of natural and synthetic wax can range from about 1 wt. % to about 40 wt. % in one aspect, from about 3 wt. % to about 20 wt. % in another aspect, and from about 5 wt. % to about 10 wt. % in a further aspect, based on the weight of the total composition.

Emulsifiers

In one aspect, the emulsifiers useful in the compositions of the invention are nonionic. Useful nonionic emulsifiers include, but are not limited to, the aliphatic ($C_6$-$C_{30}$) fatty alcohols, alkoxylated fatty alcohols, and ethoxylated sterols disclosed above, alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers; and mixtures thereof.

Other suitable nonionic emulsifiers include mono- or dialkyl alkanolamides; alkyl polyglucosides (APGs); sorbitan fatty acid esters (e.g., sorbitan laurate, sorbitan stearate); polyoxyethylene sorbitan fatty acid esters (e.g., Polysorbate-20, Polysorbate-40, Polysorbate-60, Polysorbate-80); polyoxyethylene acids, and polyoxyethylene alcohols. Other examples of suitable nonionic surfactants include coco mono- or diethanolamide, coco glucoside, decyl diglucoside, lauryl diglucoside, coco diglucoside, cetearyl alcohol, lanolin alcohol, stearic acid, glyceryl stearate, PEG-100 stearate, laureth-7, and oleth-20; Hydrogenated Castor Oil, PEG-40 Hydrogenated Castor Oil, PEG-50 Hydrogenated Castor Oil, PEG-60 Hydrogenated Castor Oil, PEG-60 Almond Glycerides, PEG-70 Mango Glycerides, PEG-192 Apricot Kernel Glycerides; and mixtures thereof.

Still other nonionic emulsifiers include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc. under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively; and mixtures thereof, are also suitable. Mixtures of any of the emulsifiers disclosed herein also are contemplated herein. The amount of emulsifier can range from about 1 wt. % to about 25 wt. % in one aspect, from about 3 wt. % to about 20 wt. % in another aspect, and from about 5 wt. % to about 15 wt. % in a further aspect, based on the weight of the total composition.

Fragrances

A variety of fragrances may be used in the compositions of the present invention. The term "fragrance" is meant to encompass any component reacting with the human olfactory sites and imparting a pleasurable odor, essence or scent. Fragrances that may be used in accordance with the present invention include any synthetic as well as natural fragrance and mixtures thereof. Typically, a multiplicity of fragrances is employed to achieve the desired scent. Fragrance base materials comprise inter alia alcohols, ketones, aldehydes, esters, ethers, nitrites, and cyclic and acyclic alkenes, especially terpenes. A further way of classifying fragrances is in accordance with generally recognized scents they produce. Descriptors used by those skilled in the art of fragrances are inter alia "rose", "floral", "green", "citrus", "spicy", "honey", "musk", "herbal", "jasmin", "lilac", lily of the valley", "orange", "peach", "oriental", "watermelon" "chypre" and "lemon", "woody", "fruity", and the like, all of which may be formulated with the compositions of the present invention. A listing of common fragrance base materials can be found in various reference sources, for example, "Perfume and Flavor Chemicals", Vols. I and II; Steffen Arctander Allured Pub. Co. (1994) and "Perfumes: Art, Science and Technology"; Muller, P. M. and Lamparsky, D., Blackie Academic and Professional (1994) both incorporated herein by reference.

Examples of synthetic fragrances that may be used in accordance with the present invention include without limitation acetanisole, acetophenone, acetyl cedrene, butylphenyl methylpropional, hydroxyisohexyl 3-cyclohexene carboxaldehyde, alpha-isomethyl ionone, methyl nonyl acetaldehyde, musk anbrette, heliotropin, citronellol, limonene, sandella, methoxycitranellal, hydroxycitranellal, phenyl ethyl acetate, phenylethylisobutarate, butylphenyl methylpropional, gamma methyl ionone, geraniol, anethole, benzaldehyde, benzyl acetate, benzyl salicylate, linalool, cinnamic alcohol, phenyl acetaldehyde, alpha-amyl cinnamic aldehyde, caphore; p-tertiary butyl cyclohexyl acetate, citral, hexyl cinnamal, cinnamyl acetate, cinnamyl alcohol, citral diethyl acetal, coumarin, ethylene brasslate, eugenol, l-menthol, vanillin, and mixtures thereof.

Examples of natural fragrances of use herein include without limitation Zingiber Officinale root extract, Melaleuca Alternifolia Leaf Oil, lavandin, heliotropin, sandlewood oil, oak moss, pathouly, ambergris tincture, ambrette seed absolute, angelic root oil, bergamont oil; benzoin Siam resin, buchu leaf oil, cassia oil; cedarwood oil, cassia oil, castoreum, civet absolute, chamomile oil, geranium oil, lemon oil, lavender oil, Ylang Ylang oil, and mixtures thereof. Mixtures of the foregoing synthetic and natural fragrances also are contemplated.

In one aspect, the composition contains less than about 2 wt. % of fragrance(s) based on the total weight of the wetting composition. In another aspect, the composition contains from about 0.01 wt. % to about 3 wt. % percent of fragrance(s). In a further aspect of the invention, the composition contains from about 0.01 wt. % to about 0.5 wt. % of fragrance(s), all based on the total weight of the composition.

Further, a variety of fragrance solubilizers may be used in the compositions of the present invention. Suitable fragrance solubilizers include, but are not limited to, benzyl benzoate, Polysorbate 20, propylene glycol, ethanol, isopropanol, diethylene glycol monoethyl ether, dipropylene glycol, diethyl phthalate, ethoxydiglycol, and triethyl citrate. In one aspect, the composition contains less than about 5 wt. % of fragrance solubilizers, from about 0.01 wt. % to about 1 wt. % in another aspect, and from about 0.01 wt. % to about 0.5 wt. % in a further aspect, based on the total weight of the composition.

Vitamins

Vitamin actives which may be used in accordance with the present invention include vitamin A and derivatives, including retinoic acid, retinyl aldehyde, retin A, retinyl palmitate, adapalene, and beta-carotene; vitamin B (panthenol, B3, provitamin B5, panthenic acid, vitamin B complex factor); vitamin C (ascorbic acid and salts thereof) and derivatives such as ascorbyl palmitate; vitamin D including calcipotriene (a vitamin D3 analog) vitamin E including its individual constituents alpha-, beta-, gamma-, delta-tocopherol and cotrienols and mixtures thereof and vitamin E derivatives including vitamin E palmitate, vitamin E linolate and vitamin E acetate; vitamin K and derivatives; vitamin Q (ubiquinone) and mixtures thereof.

Vitamins can be present in an effective amount necessary to deliver the intended therapeutic effect. In another aspect, the vitamin agent can be present in the formulation in an amount from about 0.001 wt. % to about 5 wt. %, from about 0.10 wt. % to about 3 wt. % in another aspect, and from about 0.5 wt. % to about 2 wt. % in a further aspect, based upon total weight of the composition.

Proteins

Any desired proteins, hydrolyzed proteins, protein derivatives, peptides, amino acids, and mixtures thereof (hereafter referred to as proteins for brevity) can be included in the compositions of the invention as a benefit agent to effect a desired benefit to the hair, skin, and scalp. Suitable proteins include, but are not limited to, natural structural hair and skin proteins, such as keratin. elastin, collagen, and reticulin, silk proteins, and the like. Suitable hydrolyzed proteins and protein derivatives include, but are not limited to, cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, soyethyldimonium ethosulfate, soyethyl morpholinium ethosulfate, and the like. Suitable amino acids include wheat amino acids and those disclosed in U.S. Pat. No. 4,201,235 and U.S. Pat. No. 7,572,933 which are incorporated herein be reference.

The amount of protein(s) suitable for use in the present compositions can be easily determined by the artisan of ordinary skill depending upon the intended therapeutic or cosmeceutical purpose. In one aspect, the amount of protein(s) can range from about 0.01 wt. % to about 10 wt. %, from about 0.1 wt. % to about 5 wt. % in another aspect, and from about 0.5 wt. % to about 3 wt. % in a further aspect, based on the total weight of the composition.

Botanicals

Optionally, the compositions of the invention can contain botanical material extracts. Extracted botanical materials can include any water soluble or oil soluble material extracted from a particular plant, fruit, nut, or seed. Suitable botanical agents can include, for example, extracts from Echinacea (e.g., sp. angustifolia, purpurea, pallida), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel, and combinations thereof. Other botanical extracts include, for example, chlorogenic acid, glutathione, glycyrrhizin, neohesperidin, quercetin, rutin, morin, myricetin, absinthe, and chamomile. The botanical actives can be present in an amount ranging from about 0.1 wt. % to about 10 wt. % in one aspect, from about 0.5 wt. % to about 8 wt. % in another aspect, and from about 1 wt. % to about 5 wt. % in a further aspect, based of the total weight of the composition.

Pharmaceutical and Cosmeceutical Actives

The compositions of the present invention can be formulated with a pharmaceutical and/or a cosmeceutical active to deliver a desired effect. Examples of such active ingredients include, but are not limited to, caffeine, anti-stretch mark compounds, astringents (e.g., alum, oatmeal, yarrow, witch hazel, bayberry, and isopropyl alcohol), draining compounds, depilatories (e.g., calcium and sodium hydroxide, calcium or sodium thioglycolate, or mixtures thereof), hair growth promoting compounds (e.g., monoxidil), skin and hair nourishing compounds (e.g., bioquinones), skin and hair protecting compounds, self-tanning compounds (e.g., mono- or polycarbonyl compounds such as, for example, isatin, alloxan, ninhydrin, glyceraldehyde, mesotartaric aldehyde, glutaraldehyde, erythrulose, tyrosine, tyrosine esters, and dihydroxyacetone), skin lighteners (e.g., kojic acid, hydroquinone, arbutin, fruital, vegetal or plant extracts, such as lemon peel extract, chamomile, green tea, paper mulberry extract, and the like, ascorbyl acid derivatives, such as ascorbyl palmitate, ascorbyl stearate, magnesium ascorbyl phosphate, and the like), lip plumping compounds, anti-aging, anti-cellulite, and anti-acne compounds (e.g., acidic agents such as alpha-hydroxy acids (ANAs), beta-hydroxy acids (BHAs), alpha amino-acids, alpha-keto acids (AKAs), acetic acid, azelaic acid, and mixtures thereof), anti-inflammatory compounds (e.g., aspirin, ibuprofen, and naproxen), analgesics (e.g., acetaminophen), antioxidant compounds, antiperspirant compounds (e.g., aluminum halides, aluminum hydroxyhalides, aluminum sulfate, zirconium (zirconyl) oxyhalides, zirconium (zirconyl)hydroxyhalides, and mixtures or complexes thereof), deodorant compounds (e.g., 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof), anti-dandruff agents (e.g., sulfur, zinc pyrithione, zinc omadine, miconazole nitrate, selenium sulfide, piroctone olamine, N,N-bis(2-hydroxyethyl)undecenamide, cade oil, pine tar, Allium cepa extract Picea abies extract, and Undecyleneth-6, and mixtures thereof); and mixtures of any of the above.

The pharmaceutical and cosmeceutical actives can be present in an amount sufficient to deliver a pharmaceutical or cosmeceutical effect, the specific amount of which can readily be determined by one skilled in the pharmaceutical and cosmeceutical art. In one aspect, the amount of pharmaceutical and/or cosmeceutical active component can range from about 0.01 wt. % to about 15 wt. % in one aspect, from about 0.5 wt. % to about 10 wt. % in another aspect, and from about 1 wt. % to about 5 wt. % in a further aspect, based of the total weight of the composition.

Pigments and Colorants

Exemplary pigments are metal compounds or semi-metallic compounds and may be used in ionic, nonionic or oxidized form. The pigments can be in this form either individually or in admixture or as individual mixed oxides or mixtures thereof, including mixtures of mixed oxides and pure oxides. Examples are the titanium oxides (e.g., $TiO_2$), zinc oxides (e.g., ZnO), aluminum oxides (for example, $Al_2O_3$), iron oxides (for example, $Fe_2O_3$), manganese oxides (e.g., MnO), silicon oxides (e.g., $SiO_2$), silicates, cerium oxide, zirconium oxides (e.g., $ZrO_2$), barium sulfate ($BaSO_4$), and mixtures thereof.

Other examples of pigments include D&C Red No. 30, D&C Red No. 36, D&C Orange No. 17, Green 3 Lake, Ext. Yellow 7 Lake, Orange 4 Lake, Red 28 Lake, the calcium lakes of D&C Red Nos. 7, 11, 31 and 34, the barium lake of D&C Red No. 12, the strontium lake D&C Red No. 13, the aluminum lakes of FD&C Yellow No. 5 and No. 6, the aluminum lakes of FD&C No. 40, the aluminum lakes of D&C Red Nos. 21, 22, 27, and 28, the aluminum lakes of FD&C Blue No. 1, the aluminum lakes of D&C Orange No. 5, the aluminum lakes of D&C Yellow No. 10; the zirconium lake of D&C Red No. 33, iron oxides, thermochromic dyes that change color with temperature, calcium carbonate, aluminum hydroxide, calcium sulfate, kaolin, ferric ammonium ferrocyanide, magnesium carbonate, carmine, barium sulfate, mica, bismuth oxychloride, zinc stearate, manganese violet, chromium oxide, titanium dioxide nanoparticles, barium oxide, ultramarine blue, bismuth citrate, hydroxyapatite, zirconium silicate, carbon black particles and the like. Other suitable particulates include various optical modifiers as described in U.S. Pat. No. 7,202,199.

Mixtures of pigments and colorants to achieve a desired product color and the amount of each pigment and colorant to utilize is up to the formulator and is well within the skill in the formulation art. In one aspect the amount of pigment and/or colorant utilized in the compositions of the invention range from about 1 wt. % to about 20 wt. %, based on the total weight of the composition.

Sunscreen Agents

A wide variety of sunscreen actives are useful herein. The exact amount and type of sunscreen that is used depends on the level of photo protection that is desired. Generally, any agent offering protection against ultraviolet radiation by absorbing, scattering or reflecting the ultraviolet radiation may be used herein. The sunscreen agents used herein may offer protection against one or more of the following forms of sunlight radiation UVA, UVB, UVC, visible light and infrared radiation. Generally, the sun protection factor (SPF) in the final formulation varies between 2 and 30, although products with SPFs up to 100 may be formulated. The sunscreen used herein may offer chemical or physical photo protection.

Sunscreens which can be used in accordance with the present invention include those selected from amino benzoic acid and derivatives, such as para-amino benzoic acid (PABA), glyceryl-PABA (Lisadimate), Padimate 0, Roxadimate; anthrinalates, including methylanthrynilate; benzophenones, including dioxybenzone, oxybenzone and sulisobenzone, 3-benzophenone (Uvinul M40) 4-N,N-dimethylaminobenzoic acid ester with 2,4-dihydroxybenzophenone; camphor derivatives including 3-(4-methylbenzylidene) camphor, 3-benzylidene camphor; cinnamates including DEA-p-methoxycinnamate, ethylhexyl p-methoxy cinnamate, octocrylene, octyl methoxy cinnamate (Parasol MCX), dibenzoyl methanes including butyl-methoxydibenzoylmethane (Parsol 1789), salicylates including, homomethyl salicylate, octyl salicylate, trolamine methyl salicylate; metal oxides including titanium dioxide, zinc oxide and iron oxide; 2-phenylbenzimidazole-5-sulfonic acid; 4,4-methoxy-t-butyldibenzoylmethane; and mixtures thereof.

The amount of sunscreen agent employed in the composition can range from about 0.5 wt. % to about 30 wt. % in one aspect, from about 1 wt. % to about 25 wt. % in another aspect, and from about 2 wt. % to about 15 wt. % in a further aspect of the invention (based upon the weight of the total sunscreen composition). The exact amounts can vary depending on the UV absorbing agent(s) chosen and the desired SPF value of the composition.

Buffering Agents

Buffering agents can be used in the compositions of the invention. Suitable buffering agents include, but are not limited to, alkali or alkali earth metal carbonates, phosphates, bicarbonates, citrates, borates, acetates, acid anhydrides, succinates, and the like, and mixtures thereof. Exemplary buffer agents include, but are not limited to, sodium phosphate, sodium citrate, sodium acetate, sodium bicarbonate, and sodium carbonate.

pH Adjusting Agents

Various acidic and basic (alkaline) materials can be utilized as a pH adjusting agent in the present invention. Acidic materials include organic and inorganic acids, as well as combinations thereof. Exemplary organic acids are, without limitation, acetic acid, citric acid, tartaric acid, alpha-hydroxy acids, beta-hydroxy acids, salicylic acid, lactic acid, glycolic acid, and natural fruit acids, and the like; and mixtures thereof. Exemplary inorganic acids, without limitation, are hydrochloric acid, nitric acid, sulfuric acid, sulfamic acid, phosphoric acid, and the like; and mixtures thereof.

Alkaline materials include organic and inorganic bases, as well as combinations thereof. Examples of organic bases include, without limitation, triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine (2-amino 2-hydroxymethyl-1,3-propanediol), PEG-15 cocamine, and the like; and mixtures thereof. Examples of inorganic bases include, without limitation, the alkali metal hydroxides (especially sodium, potassium, and ammonium), and alkali metal salts of inorganic acids, such as sodium borate (borax), sodium phosphate, sodium pyrophosphate, and the like; and mixtures thereof.

The pH adjusting agent(s) and/or buffering agent(s) is/are utilized in any amount necessary to obtain and/or maintain a desired pH value in the composition.

Sheen Enhancing Agents

Sheen enhancing agents also known as glossifiers improve the sheen of fixative films when applied to a hair style. An exemplary sheen enhancer suitable for use in the hair styling compositions of the invention include the non-volatile aryl-silicone fluids such as, for example, Phenyl Trimethicone and Diphenyl Dimethicone marketed by Dow Corning as Dow Corning® 556, and Rhodia, Inc. as Mirasil® DPDM, respectively. The Guerbet esters described herein also function as sheen or gloss enhancers. Guerbet esters are commercially available from Lubrizol Advanced Materials, Inc. under product designations G-20, G-36, G-38, and G-66. Murumuru butter also can be utilized as a sheen enhancing agent. In one aspect, the sheen enhancing agent, alone or in combination, typically comprises from about 1 wt. % to about 20 wt. % of the hair styling composition, from about 2 wt. % to about 15 wt. % in another aspect, and from about 3 wt. % to about 10 wt. % in a further aspect, based on the total weight of the hair styling composition.

Hair Colorants

The polymers of the invention can be utilized in the formulation of temporary, semi-permanent, or permanent hair color styling gels. The composition of the invention can contain a hair dye selected from thermochromic dyes, neutral acid or cationic nitrobenzene dyes, neutral acid or cationic azo dyes, quinone dyes, neutral, acid or cationic anthraquinone dyes, azine dyes, triarylmethane dyes, indoamine dyes and natural dyes. In one aspect of the invention, cationic dyes are utilized. Such dyes are generally known to the art and to the literature and are commonly described in two different manners. The dye name (e.g., Basic Brown 16) relates to its INCI name (International Nomenclature Cosmetic Ingredient) and/or its CTFA name (Cosmetic, Toiletry and Fragrance Association) name. These dyes also are referenced through the Color Index No. (e.g., CI 12250) which is used by the European Union. Both sets of numbers are set forth in the "International Cosmetic Ingredient Dictionary and Handbook" for example, the 7$^{th}$ Edition, 1997, published by The Cosmetic, Toiletry, and Fragrance Association, Washington, D.C., U.S.A. Specific cationic dyes which can be utilized include, but are not limited to, the various azo dyes such as Basic Brown 16 (CI 12250), Basic Brown 17 (CI 12251), Basic Red 76 (CI 12245), Basic Yellow 57 (CI 12719), as well as various anthraquinone dyes such as Basic Blue 99 (C156059), and the like. The dye or dyes can be present in a concentration from about 0.001 wt. % to about 20 wt. % in one aspect, from about 0.005 wt. % to about 10 wt % in another aspect, and from about 0.1 wt. % to about 5 wt. % in a further aspect, based upon the total weight of the composition.

Electrolytes

Electrolytes or electrolyte salts are generally known to reduce the viscosity obtained with conventional carbomer polymer thickeners. The compositions of this invention also can contain electrolytes as a viscosity modifier to adjust the viscosity of the hair styling or personal care composition. The electrolyte salts include, but are not limited to aluminum chlorohydrate and the alkali metal salts, e.g., sodium, potassium or lithium salts, these salts preferably being halides, such as the chloride. Exemplary alkali metal halide salts include, but are not limited to sodium chloride, potassium chloride, lithium chloride, and mixtures thereof. The amount of electrolyte that can be included in the composition ranges from about 0.1 wt. % to about 3 wt. % in one aspect, from about 0.5 wt. % to about 2 wt. % in another aspect, and from about 0.6 wt. % to about 1 wt. % in further aspect of the invention, based on the total weight of the composition.

Oxidizing and Reducing Agents

The compositions of the invention can include oxidizing and/or reducing agents. The oxidizing agent can be selected from the hydrogen peroxide, urea peroxide, alkali metal bromates, ferricyanides, persalts, and redox enzymes, optionally with their respective donor or cofactor. The reducing agent can be selected from thiols, like cysteine, thioglycolic acid, thiolacetic acid, their salts and esters, cysteamine, and its salts or sulfites. In the case of compositions intended for bleaching, ascorbic acid, its salts and its esters, erythorbic acid, its salts and its esters, and sulfinates, such as, sodium hydroxymethanesulfinate. The amount of oxidizing and/or reducing agent can range from about 0.01 wt. % to about 30 wt. % in one aspect, from about 0.05 wt. % to about 20 wt. % in another aspect, and from about 0.1 wt. % to about 5 wt. % in a further aspect, based on the total weight of the composition.

Chelating Agents

Chelating agents can be employed to stabilize the compositions of the invention against the deleterious effects of metal ions and UV radiation (e.g., sunlight). When utilized, suitable chelating agents include EDTA (ethylene diamine tetraacetic acid) and salts thereof such as disodium EDTA, citric acid and salts thereof, cyclodextrins, and the like, and mixtures thereof. The chelating agents typically comprise about 0.001 wt. % to about 3 wt. % in one aspect, from about 0.01 wt. % to about 2 wt. % in another aspect, and from about 0.01 wt. % to about 1 wt. % in a further aspect of the total weight of the compositions of the present invention.

Insoluble Components

Cosmetic beads, flakes, capsules, powders, particulates (e.g., micronized silica), gas bubbles, and combinations thereof can be included in the composition for aesthetic appearance or can function as micro- and macro-encapsulants for the delivery of benefit agents (e.g., vitamins, conditioners, moisturizers, etc.) to the scalp and hair. Exemplary bead components include, but are not limited to, agar beads, alginate beads, jojoba beads, gelatin beads, Styrofoam™ beads, polyacrylate, polymethylmethacrylate (PMMA), polyethylene beads, Unispheres™ and Unipearls™ cosmetic beads (Induchem USA, Inc., New York, N.Y.), Lipocapsule™, Liposphere™, and Lipopearl™ microcapsules (Lipo Technologies Inc., Vandalia, Ohio), and Confetti II™ dermal delivery flakes (United-Guardian, Inc., Hauppauge, N.Y.). Aesthetic bubbles of air or an inert gas can be incorporated into the compositions of the invention by well known techniques. The amount of insoluble component(s) that is incorporated into the compositions of the invention will depend upon the desired aesthetic property the formulator is conveying with the end product. Any amount of insoluble component can be utilized as long as the rheology and fixative properties of the composition are not deleteriously affected. In one aspect, the compositions of the invention can contain from about 0.1 wt. % to about 10 wt. %, from about 0.5 wt. % to about 5 wt. % in another aspect, and from about 3 wt. % to about 5 wt. % in a further aspect based on the total weight of the composition.

Preservatives

Any preservative suitable for use in personal care products, can be used in the compositions of the present invention. In one aspect, suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds disclosed above (e.g., Polyquaternium-1).

In another aspect, acid based preservatives are useful in the compositions of the present invention. In one aspect, the acid preservative is a carboxylic acid compound represented by the formula: $R^{53}C(O)OH$, wherein $R^{53}$ represents hydrogen, a saturated and unsaturated hydrocarbyl group containing 1 to 8 carbon atoms or $C_6$ to $C_{10}$ aryl. In another aspect, $R^{53}$ is selected from hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

In another aspect, suitable acids include but are not limited to, oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and mixtures thereof.

Salts of the foregoing acids are also useful as long as they retain efficacy at low pH values. Suitable salts include the alkali metal (e.g., sodium, potassium, calcium) and ammonium salts of the acids enumerated above. An example of a suitable alkali metal salt preservative is sodium benzoate.

The preservatives typically comprise from about 0.01 wt. % to about 3.0 wt. % in one aspect, from about 0.1 wt. % to about 1 wt. % in another aspect, and from about 0.3 wt. % to about 1 wt. % by weight in a further aspect, based on the total weight of the compositions of the present invention.

In other embodiments, the hair fixative compositions may be in the form of an aerosol or non-aerosol spray, a mousse or a hair-setting lotion. The compositions may be aqueous, i.e., they are substantially free of organic solvents, or non-aqueous, although aqueous hair fixative compositions are preferred. The compositions may contain up to 40 weight percent, preferably up to 35 weight percent, of propellants, such as ethers, compressed gases, halogenated hydrocarbons and hydrocarbons. Exemplary propellants are dimethyl ether, propane, butane and 1,1-difluoroethane. Non-aerosol hair fixative compositions may further include solvents such as ethanol, isopropanol, acetone, dimethoxymethane and methyl ethyl ketone. In one aspect, the solvent in such non-aerosol compositions can be present in an amount ranging from 10 wt. to about 70 wt. %, from about 20 wt. % to about 60 wt. % in another aspect, and from about 25 wt. % to 50 wt.

% in a further aspect, based on the total weight of the composition. Such propellants, solvents and materials or additives are commonly used in hair fixative compositions known heretofore.

Mousses according to the present invention comprise an amount of the polymer which is effective to impart hair fixative properties to the mousse, similar to gel fixatives. The mousses further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation: Nonoxynol 15) and Brij 97 (INCI designation: Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water.

If desired, the clarity and appearance of the hair styling gel or personal care compositions of the invention can be adjusted. The clarity of the gel may vary from substantially transparent with little visual haze where insoluble component additives such as beads, air bubbles, pearlizing agents, are clearly visible to visually opaque. Visually distinct, multiple phase compositions where one phase is clear and another phase is opaque are also envisioned. In one embodiment of the hair gel, a pattern comprising phases that are visually distinct from each other may be formed by mixing clear and opaque components. The visual distinction between the phases can be in color, texture or the type of insoluble component contained therein. The specific pattern can be chosen from a wide variety of patterns, including, but not limited to striping, marbling, geometrics, spirals, and combinations thereof. Compositions of this invention demonstrate excellent stability with time in suspending insoluble components and stabilizing visually distinct phases.

The polymers of the invention in addition to the hair fixative applications can usefully be employed for cosmetic purposes as film formers, skin barriers, skin protectants (e.g., sunscreens, sun block, barrier creams), pigmented skin colorants (e.g., face and body makeups, foundation creams, mascara, rouge, lip products, and the like), and can be formulated with any of the ingredients disclosed herein as well as with other ingredients known to the cosmetic industry and registered under CTFA International Cosmetic Ingredients Dictionary and Handbook.

This invention is illustrated by the following examples that are merely for the purpose of illustration and are not to be regarded as limiting the scope of the invention or the manner in which it can be practiced. Unless specifically indicated otherwise, parts and percentages are given by weight.

Methods

Specific Viscosity

The specific viscosity of polymers of the invention is measured in DMSO solvent at 25.5° C. using a Cannon-Ubbelohde viscometer No. 1C (Cannon Instrument Company, State College, Pa.). 1.0000 g of dry polymer and 100 g of DMSO (dimethyl sulfoxide) solvent are weighed into a 4 oz jar and mixed at moderate speed using magnetic stirrer at about 90° C. for about 5 hours. The solution is filtered through 75 micron nylon filter into a 4 oz clean jar to remove any undissolved material or gel particles. The Ubbelohde viscometer is rinsed twice before filling with DMSO and placed in a constant temperature bath (25.5° C.) to attain thermal equilibrium. The DMSO solvent is then gently pulled above the upper graduation mark by applying suction to the suction arm opposite the capillary tube. The time for the solution to flow from the upper to lower graduation marks is recorded. The average of three efflux readings for the solvent, DMSO, is recorded as $\eta_s$. This procedure is repeated for the polymer solution and recorded as $\eta$. The relative viscosity ($\eta_{rel}$) is the ratio of the viscosity of the polymer solution of the solvent ($\eta_s$) (ASTM D 2857-95 2007). The specific viscosity ($\eta_{sp}$) is the relative viscosity of a polymer solution of known concentration minus (1). Relative viscosity and specific viscosity are calculated by the equations:

Relative Viscosity($\eta_{rel}$)=$\eta/\eta_s$

Specific Viscosity($\eta_{sp}$)=$\eta_{rel}$−1

Additional details of the polymer solution properties can be obtained from the reference, Textbook of Polymer Chemistry, Billmeyer, Interscience Publishers, New York, 1957, pages 125-139.

Mechanical Stiffness Test

A TA XTPlus Texture Analyzer (Stable Micro Systems, Surrey, UK) fitted with a rectangular loading nose (3 mm thick×70 mm wide×99 mm high) and a 3-point bending rig is employed to evaluate the mechanical stiffness of a fixative treated hair tress. The texture analyzer is interfaced with a personal computer loaded with Texture Exponent 32 data acquisition software that collects and analyzes the data inputted from the instrument. The bending rig consists of two parallel support legs that are spaced apart by approximately 25.4 mm. The treated hair swatch test sample is centered across the span of the support legs and the loading nose which is centered above and between the support legs is pressed through the sample at a rate of 40 mm/s for a distance of 20 mm. Data acquisition starts when the loading nose contacts the sample. The data acquisition software calculates and records the amount of force (Newtons) required to deflect the sample through a distance of 20 mm. The results are reported as Peak Force (N).

Hair swatches (6.5" long, 2.5 g in weight) consisting of virgin natural human hair are bound with a flat (sewn and waxed) binding so that the tress has a uniform rectangular cross section along its whole length. The tresses are washed with a stripping shampoo containing 10 wt. % ammonium lauryl sulfate and rinsed with deionized water. A designated amount of experimental fixative (0.8 g) is evenly applied to the damp hair swatches. The treated swatches are laid flat on Teflon® foil to dry at 23° C. and 50% relative humidity in a controlled laboratory environment for 16 hours and evaluated for stiffness. A subjective rating is assigned to the specific ranges of Peak Force (N) to classify the stiffness of the fixative polymer as follows:

| Mechanical Stiffness Average Peak Force (Newtons) | Stiffness Subjective Rating |
| --- | --- |
| <1 | Soft (untreated hair swatch) |
| <3 | Soft-Flexible Hold |
| 3-4 | Soft Slightly Hard hold |
| 4-5 | Slightly Hard Hold |
| 5-6 | Hard Hold |
| 6-7 | Very Hard Hold |
| >7 | Ultra Hard Hold |

Gel Property Testing

Rheological gel property measurements (short flow and long flow) are conducted on a controlled stress rheometer (TA instruments AR 1000N rheometer, New Castle, Del.). Short flow rheology is characterized as a gel consistency similar to that of mayonnaise. In practice, gels exhibiting short flow rheology maintain their static state structural integrity and do not run or flow from opened product containers such as tubes and wide mouth jars when inverted, or do not run down the fingers prior to application to the hair. In contrast, long flow rheology is characterized as a gel consistency similar to that of honey. Gels exhibiting long flow rheology do not maintain their static state structural integrity when not confined by a container. Such gels readily flow from opened and inverted product containers and tend to run down the fingers as they are being applied to the hair.

The controlled stress rheometer in oscillation mode is used to evaluate the flow characteristics of gel mucilages (4 wt. % total polymer solids in water neutralized to pH 7.0. The rheometer is equipped with cone and plate probe utilizing a 40 mm, 2° cone set at a 56 μm gap. Testing is conducted at 23° C. Test samples are allowed to equilibrate for 18 min. following sample loading before testing is conducted. Programmed oscillation stress (shear stress) sweeps of 0.1 to 6,000 Pa at a frequency of 1 Hz are conducted on the test sample and analyzed via Rheology Data Analysis software (version 5.1) to determine the "break point" of the gel. By gradually increasing the oscillation stress on a gel sample the break point can be determined by observing the oscillation stress at which there is a decay (5% drop) of G' (elastic modulus). The break point is an indication of the shear thinning ability of the gel. A high value for oscillation stress at the break point indicates that a larger oscillation stress (shear stress) value is needed to break down the gel structure and is more resistant to flow. On the other hand, a gel which has a break point at a lower oscillation stress value is less resistant to flow. Gels with a lower G' values (<100 Pa) tend to flow readily and are characterized as long flow gels. Gels with larger G' values 100 Pa) tend to be flow resistant and are characterized as short flow gels.

Viscosity

Brookfield rotating spindle method (all viscosity measurements reported herein are conducted by the Brookfield method whether mentioned or not): The viscosity measurements are calculated in mPa·s, employing a Brookfield rotating spindle viscometer, Model RVT (Brookfield Engineering Laboratories, Inc.), at about 20 revolutions per minute (rpm), at ambient room temperature of about 20 to 25° C. (hereafter referred to as viscosity). Spindle sizes are selected in accordance with the standard operating recommendations from the manufacturer. Generally, spindle sizes are selected as follows:

| Spindle Size No. | Viscosity Range (mPa · s) |
| --- | --- |
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. The artisan of ordinary skill in the art will select a spindle size appropriate for the system to be measured.

Yield Value

Yield Value, also referred to as Yield Stress, is defined as the initial resistance to flow under stress. It is measured by the Brookfield Yield Value (BYV) Extrapolation Method using a Brookfield viscometer (Model RVT) at ambient room temperature of about 20 to 25° C. The Brookfield viscometer is used to measure the torque necessary to rotate a spindle through a liquid sample at speeds of 0.5 to 100 rpm. Multiplying the torque reading by the appropriate constant for the spindle and speed gives the apparent viscosity. Yield Value is an extrapolation of measured values to a shear rate of zero. The BYV is calculated by the following equation:

$$BYV, dyn/cm^2 = (\eta_{\alpha 1} - \eta_{\alpha 2})/100$$

where $\eta_{\alpha 1}$ and $\eta_{\alpha 2}$=apparent viscosities obtained at two different spindle speeds (0.5 rpm and 1.0 rpm, respectively). These techniques and the usefulness of the Yield Value measurement are explained in Technical Data Sheet Number 244 (Revision: 5/98) from Noveon Consumer Specialties of Lubrizol Advanced Materials, Inc., herein incorporated by reference.

Clarity Testing

The clarity of the polymer containing gel composition is measured in % T (transmittance) by Brinkmann PC 920 calorimeter at least about 24 hours after the composition is made. Clarity measurements are taken against deionized water (clarity rating of 100%). Gel compositions having a clarity value of about 60% (T) or more are substantially clear. Gel compositions having a clarity value in the range of about 45 to 59% (T) are substantially translucent.

Flaking Evaluation Test

Flaking is assessed by inspecting treated hair swatches for a visible deposit (coating) on the hair surface and by combing the length of the treated swatch for 1 repetition, 5 repetitions and 10 repetitions with a fine tooth hard rubber comb. After each set of combing repetitions, the tines of the comb are visually inspected for polymer residue and rated as follows:

No residue on comb or hair=5
Trace of residue on comb only=4
Very slight amount of residue on comb only=3
Slight amount of residue on comb only=2
Slight amount of residue on comb and hair=1
Very visible coating of residue on comb and hair (hair is dull)=0

The test hair swatches (6.5" long, 2.5 g in weight) consisting of virgin European or Asian hair are bound with a flat (sewn and waxed) binding so that the swatch has a uniform rectangular cross section along its whole length (a ribbon-like configuration). The swatches are washed with a stripping shampoo containing 10 wt. % ammonium lauryl sulfate and rinsed with deionized water. A designated amount of hair gel (0.8 g) is evenly applied to the damp hair swatches. The swatches are laid flat on Teflon® foil to dry at 23° C. and 50% relative humidity for 16 hours and evaluated for flaking.

High Humidity Spiral Curl Retention Test (HHSCR)

Tresses of commercially blended untreated (virgin) human hair are prepared employing natural brown or black color European and/or Oriental hair supplied by International Hair Importers and Products Inc., New York. Each hair tress (about 0.5 grams weight) is about 7.5 inches in length and is crimped (by the root portion) within a metal clamp equipped with a wire hanger loop. Prior to use, each tress is washed with a dilute aqueous solution of sodium lauryl sulfate (10% SLS) followed by thorough rinsing with deionized water at ambient room temperature. The tresses are dried by towel blotting. The initial extended length of the hair tress ($L_e$) is measured and recorded. A designated amount of hair gel (0.05 g) to be evaluated is applied to each hair tress. The polymer fixative composition to be evaluated is applied to the hair tress and distributed uniformly from the root portion of the hair to tip portion. Each treated tress is wrapped around a spiral perm rod (Cyber Sprials™ large spiral curling rods, 8 mm inner diameter, 13.5 mm outer diameter, 162 mm length, American Discount Beauty Supply, 269 South Beverly Drive #250, Beverly Hills, Calif.) and dried for 12 hours at ambient room temperature of about 21 to 23° C. After drying, the spiral perm rod is carefully removed, leaving the hair tress styled into a single spiral, and the initial length of the spiral hair curl ($L_i$) is measured and recorded. The spiraled hair tress is vertically hung in a humidity chamber set at a temperature of about 26° C. and a relative humidity level of 90%.

High humidity spiral curl retention is determined by measuring the length of the spiral hair curl as the curl relaxes. Measurements are taken at selected intervals of time ($L_t$) over a 24 hour continuum of exposure to high humidity. The following equation is used to calculate percent curl retention, relative to the initial curl length ($L_i$) and length of the fully extended hair, before curling ($L_e$):

% HHSCR=$L_e$-$L_t$/$L_e$-$L_i$×100

A curl retention of about 70% or more for a minimum period of about 0.75 hours at about 90% RH is a conventional benchmark for good high humidity resistance, and an HHSCR greater than 70% after a period of at least about 3 hours is deemed very good to excellent.

Abbreviation and Trade Name List

The monomers and components listed in the table below are utilized in the Examples of the present invention.

| | Monomers |
|---|---|
| AA | Acrylic acid |
| ACE | ACE ™ Hydroxyl acrylate monomer is the reaction product of acrylic acid with Cardura ™. Cardura is the glycidyl ester of VERSATIC ™ acid 10, a highly branched saturated carboxylic acid containing 10 carbon atoms |
| nBA | n-Butyl Acrylate |
| tBAM | t-Butyl Acrylamide |
| EA | Ethyl Acrylate |
| 2-EHA | 2-Ethylhexyl Acrylate |
| HEMA | Hydroxyethyl Methacrylate |
| MA | Methyl Acrylate |
| MAA | Methacrylic Acid |
| NVP | N-vinyl Pyrrolidone |
| STY | Styrene |
| TEGDMA | Triethyleneglycol Dimethacrylate (crosslinker) |
| TMPDAE | Trimethylolpropane Diallyl ether (crosslinker) |
| TMPTA | Trimethylolpropane Triacrylate (crosslinker) |
| TMPEO15TA | Trimethylolpropane Triacrylate, ethoxylated-15 (crosslinker) |
| VND | Vinyl Neodecanoate |

| | Components |
|---|---|
| Acrylates/C10-30 Alkyl Acrylate Crosspolymer | INCI definition: a copolymer of C10-30 alkyl acrylate and one or more monomers of acrylic acid, methacrylic acid or one of their simple esters crosslinked with an allyl ether of sucrose or an allyl ether of pentaerythritol. |
| Acrylates/Beheneth-25 Methacrylate Copolymer | INCI definition: a copolymer of the ester of methacrylic acid and Beheneth-25 and one or more monomers of acrylic acid, methacrylic acid, or one of their simple esters, Lubrizol Advanced Materials, Inc. |
| Acrylates Copolymer, | INCI definition: a copolymer of two or more monomers consisting of acrylic acid, methacrylic acid or one of their simple esters. |
| AMP-95 Ultra PC ™ 2000 | 2-methyl-2-amino-1-propanol (95 wt. % in water), Angus Chemical Company |
| Beeswax | Beeswax (Beeswax White Pure, batch # 481) |
| Carbomer | INCI definition: a homopolymer of acrylic acid crosslinked with an allyl ether of pentaerythritol, an allyl ether of sucrose, or an allyl ether of propylene. |
| Carbopol ® Aqua SF-1 | INCI Name: Acrylates Copolymer (an emulsion copolymer of two or more monomers consisting of acrylic acid, methacrylic acid or one of their simple esters), Lubrizol Advanced Materials, Inc. |
| Carbopol ® 980 | INCI Name: Carbomer, Lubrizol Advanced Materials, Inc. |
| Carbopol ® Ultrez 10 | INCI Name: Carbomer, Lubrizol Advanced Materials, Inc. |
| Carbopol ® Ultrez 20 | INCI Name: Acrylates/C10-30 Alkyl Acrylate Crosspolymer, Lubrizol Advanced Materials, Inc. |

| | Monomers |
|---|---|
| Carbopol ® Ultrez 21 | INCI Name: Acrylates/C10-30 Alkyl Acrylate Crosspolymer, Lubrizol Advanced Materials, Inc. |
| Fixate ™ G-100 | INCI Name: AMP-Acrylates/Allyl Methacrylate Copolymer; INCI definition: aminomethylpropanol salt of a copolymer of allyl methacrylate and one or more monomers consisting of acrylic acid, methacrylic acid or one of their simple esters, Lubrizol Advanced Materials, Inc. |
| Luvimer ® Pro 55 | INCI Name: Acrylates Copolymer, BASF. |
| Luvimer ® 100 P | INCI Name: Acrylates Copolymer, BASF. |
| Phenonip ™ | Blend of phenoxyethanol, methylparaben, ethylparaben, propylparaben, butylparaben and isobutylparaben, (antibacterial), Clariant Corporation-Nipa Laboratories |

| | -continued |
|---|---|
| Polyacrylate-14 | INCI definition: a copolymer of PEG-25 C10-30 alkyl ether methacrylate, PEG/PPG-5/5 allyl ether and one or more monomers consisting of acrylic acid, methacrylic acid or one of their simple esters, Lubrizol Advanced Materials, Inc. |
| Rheocare ™ TTN2 | INCI Name: Acrylates Copolymer, Cognis Corporation. |

Example 1

Into an agitator equipped first reactor containing 112.0 grams of deionized water (D.I.) and 13.33 grams of sodium lauryl sulfate (30% active in water wt./wt.), 260.8 grams of ethyl acrylate, 138 grams of methacrylic acid, 0.6 grams of trimethylolpropane triacrylate, and 0.2 grams of trimethylolpropane diallyl ether are added under nitrogen atmosphere and mixed at 900 rpm to form a monomer emulsion. To an agitator equipped second reactor are added 620 grams of deionized water and 1.27 grams of sodium lauryl sulfate (30% active in water wt./wt.). The contents of the second reactor are heated with mixing agitation (300 rpm) under a nitrogen atmosphere. When the contents of the second reactor reaches a temperature of approximately 90° C., 10.0 grams of an ammonium persulfate solution (2.0% aqueous solution wt./wt.) is injected into the heated surfactant solution. The monomer emulsion from the first reactor is gradually metered at a feed rate of 3.67 g/min. into the second reactor over a period of 150 minutes at a reaction temperature maintained at approximately 90° C. With the emulsion monomer feed, 0.3% ammonium persulfate solution (aqueous solution wt./wt.) is simultaneously metered into the reaction mixture in the second reactor. After completion of the monomer addition the resulting reaction mixture is held at a temperature of about 90° C. for an additional two and half hours to complete the polymerization. The resulting polymer emulsion product is cooled to room temperature, discharged from the reactor and recovered. The monomer components and amounts utilized are set forth in Table 1.

TABLE 1

| Ex. No. | EA | MAA | TMPTA | TMPDAE | Specific Viscosity |
|---|---|---|---|---|---|
| 1 | 65.30 | 34.5 | 0.15 | 0.05 | 3.50 |

Examples 2 to 15

The following crosslinked acrylic copolymers are polymerized in accordance with the procedure and conditions set forth in Example 1 from the monomer components set forth in Table 2. The specific viscosity of each polymer is determined and recorded in Table 2.

TABLE 2

| Ex. No. | Monomer Components (wt. %) | | | | | | | | | | | | | | Specific Viscosity $(\eta_{sp})$ |
|---|---|---|---|---|---|---|---|---|---|---|---|---|---|---|---|
| | EA | MAA | AA | STY | ACE | n-BA | VND | t-BAM | MA | NVP | HEMA | MMA | TMPTA | TMPDAE | |
| 2 | 62.75 | 37.00 | | | | | | | | | | | 0.15 | 0.10 | 2.61 |
| 3 | 65.25 | 32.50 | 2.0 | | | | | | | | | | 0.15 | 0.10 | 2.62 |
| 4 | 62.30 | 34.50 | | 3.0 | | | | | | | | | 0.15 | 0.05 | 3.33 |
| 5 | 62.30 | 34.50 | | | 3.0 | | | | | | | | 0.15 | 0.05 | 3.56 |
| 6 | 62.30 | 34.50 | | | | 3.0 | | | | | | | 0.15 | 0.05 | 3.41 |
| 7 | 62.30 | 34.50 | | | | | 3.0 | | | | | | 0.15 | 0.05 | 3.63 |
| 8 | 65.29 | 34.50 | | | | | | | | | | | 0.15 | 0.06 | 3.61 |
| 9 | 62.30 | 34.50 | | | | | | 3.0 | | | | | 0.15 | 0.05 | 3.08 |
| 10 | 64.80 | 25.00 | | | | | | | 10.0 | | | | 0.15 | 0.05 | 2.97 |
| 11 | 62.30 | 34.50 | | | | | | | | 3.0 | | | 0.15 | 0.05 | 3.90 |
| 12 | 54.80 | 45.00 | | | | | | | | | | | 0.15 | 0.05 | 3.00 |
| 13 | 59.80 | 30.00 | | | | | | | | | 10.0 | | 0.15 | 0.05 | 3.73 |
| 14 | 56.80 | 33.00 | | | | | | | 5.0 | | | 5.0 | 0.15 | 0.05 | — |

Comparative Examples C1 to C4

Comparative polymers are polymerized from the monomers set forth in Table 3 utilizing the methods and conditions previously set forth in Example 1. The specific viscosity of each polymer is determined and recorded in Table 3. The specific viscosities of commercially available fixative polymers also are determined and recorded.

TABLE 3

| Ex. No. | Monomer Components (wt. %) | | | | | Specific Viscosity $(\eta_{sp})$ |
|---|---|---|---|---|---|---|
| | EA | MAA | TMPTA | TEGDMA | TMPEO15TA | |
| C1 | 65.5 | 34.5 | — | — | — | 10.89 |
| C2 | 65.3 | 34.5 | 0.2 | — | — | 8.10 |
| C3 | 65.3 | 34.5 | — | 0.2 | — | 12.56 |
| C4 | 65.3 | 34.5 | — | — | 0.2 | 9.90 |

Commercial Fixative Polymers

| Ex. No. | Trade Name | Polymer Class | Specific Viscosity |
|---|---|---|---|
| C5 | Luvimer Pro 55 | Anionic | 0.15 |
| C6 | Luvimer 100 P | Anionic | 0.27 |
| C7 | Fixate G-100 | Anionic | 0.51 |
| C8 | Rheocare TTN2 | Anionic | 8.16 |

Example 16

Rheological gel property characterization of gels made from the polymers of Examples 6 and 8 are conducted as described in the gel property determination methodology described above and recorded in Table 4 below. In addition, gel property characterization of comparative polymers C2 to C4, and commercially available fixative polymer C7 are conducted. All of the gels are 4 wt. % total polymer solid mucilages in water neutralized to pH 7.2 with AMP-95.

TABLE 4

| Polymer No. | G' (Pa) | Gel Property | Break Point (Oscillation Stress, Pa) | Shear Thinning Ability |
|---|---|---|---|---|
| C2 | 43.95 | Long flow | 7.9 | Easy |
| C3 | 9.25 | Long flow | 3.98 | Easy |
| C4 | 43.95 | Long flow | 7.94 | Easy |
| C7 | 0.023 | Long flow | 1.25 | Easy |

TABLE 4-continued

| Polymer No. | G' (Pa) | Gel Property | Break Point (Oscillation Stress, Pa) | Shear Thinning Ability |
|---|---|---|---|---|
| Ex. 6 | 332.9 | Short flow | 12.59 | Easy |
| Ex. 8 | 216.3 | Short flow | 25.12 | Easy |

Gels containing the polymers of the invention (Examples 6 and 8) exhibit a G' of ≥100 Pa, an indication of desirable short flow rheology. Gels containing the polymers of comparative examples C2, C4, C5, and C7 demonstrate undesirable long flow rheology.

Example 17

This example compares the gel rheology, gel aesthetics, and gel properties of gels made from the polymers of Examples 1 to 13 having specific viscosities ($\eta_{sp}$) ranging from 1 to 8 with gels made from comparative polymers having specific viscosities <1 and >8. The gels are made as mucilages of 4 wt. % total polymer solids in water and neutralized to pH values ranging from 6.4 to 7.2 with AMP-95. Gel rheology properties (Brookfield viscosity, yield value, and specific viscosity), gel properties (short flow and long flow), and gel aesthetics (clarity, texture, and appearance) are measured or visually evaluated and listed in Table 5. The gel rheological properties are measured after the gels are aged for 24 hrs.

Gel properties are visually evaluated and rated as follows:

Short Flow (SF) —mayonnaise like consistency; unconfined gels maintain static state structural integrity.

Long Flow (LF)—honey like consistency; unconfined gels flow and do not maintain static state structural integrity.

Runny Flow (R)—water like consistency (viscosity <2000 mPa·s)

Gel texture is visually evaluated and rated as follows:

Smooth (S)—no lumps or gel particles; excellent shear thinning rheology with even spreadability.

Gelatin (J)—gelatin like consistency; deficient shear thinning rheology (forms clumps with applied shear).

TABLE 5

| Polymer Ex. No. | Specific Viscosity ($\eta_{sp}$) | pH | Viscosity (mPa·s) | Yield Value (dynes/cm$^2$) | Clarity (% T) | Gel Texture & Appearance |
|---|---|---|---|---|---|---|
| 1 | 3.50 | 6.99 | 14,700 | 1330 | 91 | S, SF |
| 2 | 2.61 | 7.12 | 24,600 | 2400 | 85 | S, SF |
| 3 | 2.62 | 7.03 | 22,600 | 2090 | 85 | S, SF |
| 4 | 3.33 | 7.26 | 15,900 | 1360 | 92 | S, SF |
| 5 | 3.56 | 7.2 | 13,200 | 960 | 92 | S, SF |
| 6 | 3.41 | 7.2 | 22,100 | 1670 | 95 | S, SF |
| 7 | 3.63 | 7.2 | 11,800 | 930 | 92 | S, SF |
| 8 | 3.61 | 7.26 | 11,300 | 940 | 97 | S, SF |
| 9 | 3.08 | 7.2 | 11900 | 960 | 93 | S, SF |
| 10 | 2.97 | 7.36 | 21500 | 2060 | 83 | S, SF |
| 11 | 3.90 | 7.14 | 10,900 | 870 | 90 | S, SF |
| 12 | 3.00 | 7.21 | 16,400 | 1240 | 89 | S, SF |
| 13 | 3.73 | 7.21 | 14,500 | 1330 | 83 | S, SF |
| C1 | 10.89 | 7.0 | 15,100 | 470 | 92.8 | R, LF |
| C2 | 8.10 | 7.08 | 9,200 | 440 | 90.4 | J, LF |
| C3 | 12.56 | 7.11 | 7,400 | 128 | 91.6 | J, LF |
| C4 | 9.90 | 7.07 | 9,350 | 394 | 92.9 | J, LF |
| C5 | 0.15 | 7.84 | 16,900 | 1,380 | opaque | S, LF |
| C6 | 0.27 | 8.07 | 1,800 | 90 | opaque | R[1] |
| C7 | 0.51 | 6.91 | 90 | 0 | 96.1 | R |
| C8 | 8.16 | 6.2 | 145,000 | 5,900 | 49.2 | J |

[1]Runny flow with chunky inclusions.

Gels prepared from the polymers of Examples 1 through 13 with specific viscosity values ($\eta_{sp}$) ranging from 1 to 8 exhibit an aesthetically pleasing smooth gel appearance and short flow rheology, whereas gels prepared from commercial polymers C5 to C8 with $\eta_{sp}$<1 give a poor performance in overall rheology properties resulting in runny and long flow (LF) appearance and other set of comparative polymers with the $\eta_{sp}$>8, give gels with undesirable gelatin like textures. Gels made from the comparative polymers C2, C3, and C4 exhibit good clarity and viscosity values but possess poor yield values (<500 dynes/cm$^2$) and low elastic modulus (G'<100 Pa), resulting in poor gel rigidity, poor aesthetic appearance, and inability to suspend insoluble components.

Example 18

The following styling gel examples formulated with the polymers of Examples 1, 4, 5, 6, 7, and 8 demonstrate good compatibility with anionic thickeners giving excellent styling properties (stiffness and humidity resistance), gel properties and gel aesthetics. The polymers are formulated at a 1 wt. % total polymer solids for a medium hold hair styling gel and at 4 wt. % total polymer solids for an ultra stiff hold hair styling gel. The polymers are formulated into styling gels containing the ingredients set forth in Table 6.

TABLE 6

| Component | Trade Name | Amount (wt. %) | Function | INCI Name |
|---|---|---|---|---|
| 1 | Deionized Water | Q.S. | Diluent | |
| 2 | Carbopol ® Ultrez 21 Polymer | 0.6 | Auxiliary Thickener | Acrylates/C10-30 Alkyl Acrylate Crosspolymer |
| 3 | Polymer (30% active polymer solids) | 1 (medium hold) or 4 (ultra hold) | Fixative/ Thickener | |
| 4 | Glydant ® Plus Liquid | 0.3 | Preservative | DMDM Hydantoin (and) Iodopropynyl Butylcarbamate |
| 5 | AMP-95 ® | QS | Neutralizer | Aminomethyl Propanol |

Deionized water is added into a 500 gram vessel and component No. 2 is sprinkled onto the surface of the D.I. water and allowed to wet. Once the powdered auxiliary thickener is wetted, the contents of the vessel are gently mixed. Component No. 3 is added into the mixture with agitation until homogenous. Component No. 4 is added, followed by neutralization with the component No. 5 and mixed until clear and homogeneous composition is attained. After resting the hair gel composition for 24 hrs. to reach equilibrium, pH, viscosity, yield value, and clarity are measured and recorded. In addition, gel properties and gel texture is visually evaluated as set forth in Example 17. Styling gel formulations containing comparative polymers C1 to C8 are identically formulated at 4 wt. % total active polymer solids to obtain ultra hold styling gels for comparative purposes. The data are presented in Table 7.

TABLE 7

| | Medium Stiffness (1 wt. % TS) | | | | | Ultra Stiffness (4 wt. % TS) | | | | |
|---|---|---|---|---|---|---|---|---|---|---|
| Polymer Ex. | pH | Viscosity (mPa·s) | Yield Value (dynes/cm²) | Clarity (% T) | Texture/Gel Properties | pH | Viscosity (mPa·s) | Yield Value (dynes/cm²) | Clarity (% T) | Texture/Gel Properties |
| 1 | 7.10 | 25,100 | 2,180 | 93.7 | S, SF | 7.1 | 33,300 | 2,800 | 91.3 | S, SF |
| 4 | 7.17 | 27,000 | 2,380 | 91.7 | S, SF | 7.07 | 41,000 | 3,240 | 85.3 | S, SF |
| 5 | 6.98 | 28,300 | 2540 | 86.2 | S, SF | 7.05 | 33,700 | 2400 | 83.1 | S, SF |
| 6 | 7.05 | 35,800 | 3460 | 91.8 | S, SF | 7.00 | 76,000 | 5280 | 81.9 | S, SF |
| 7 | 6.96 | 24,700 | 2120 | 93.6 | S, SF | 6.91 | 34,600 | 2580 | 88.9 | S, SF |
| 8 | 7.0 | 22,000 | 1,800 | 95.1 | S, SF | 7.0 | 28,700 | 2,450 | 94.5 | S, SF |
| C1 | — | — | — | — | — | 7.0 | 15,100 | 470 | 92.8 | LF |
| C2 | — | — | — | — | — | 7.08 | 17,900 | 1060 | 93.1 | J, LF |
| C3 | — | — | — | — | — | 7.06 | 12,400 | 470 | 94.4 | R |
| C4 | — | — | — | — | — | 6.99 | 17,800 | 1040 | 94.1 | LF |
| C5 | — | — | — | — | — | 7.84 | 16,900 | 1,380 | opaque | S, LF |
| C6 | — | — | — | — | — | 8.07 | 1,800 | 90 | opaque | R[1] |
| C7 | — | — | — | — | — | 6.91 | 90 | 0 | 96.1 | R |
| C8 | — | — | — | — | — | 6.2 | 145,000 | 5,900 | 49.2 | J |

[1]Runny flow with chunky inclusions.

Example 19

Styling gel compositions having hard hold to ultra hard hold stiffness properties with high humidity resistance are formulated with the polymer of Example 1. The compositions are identically formulated as described in Example 18 (with and without auxiliary thickener) and prepared at the polymer solids levels set forth in Table 8. The data in Table 8 demonstrate that the formulated gels have increased clarity while maintaining a good viscosity profile (not too viscous or too runny). Both stiffness and humidity resistance testing are conducted as described in the methodology above (the standard deviation for the reported data is also set forth in the table). Enhanced stiffness properties are attained with powdered anionic copolymer auxiliary thickeners (Acrylates/C10-30 Alkyl Acrylate Crosspolymer).

TABLE 8

| Polymer Ex. No. | Polymer Solids (wt. %) | Auxiliary Thickener (wt. %) | Viscosity (mPa·s) | Clarity (% T) | Stiffness (N) @ 50% RH | HHSCR (%) after 8 hrs |
|---|---|---|---|---|---|---|
| 6 | 1 | 0.0 | 3,100 | 84.5 | 5.6 (+/−0.7) (HH) | 73.8 (+/−3.0) (Pass) |
| | 1 | 0.6 | 21,750 | 94.5 | 7.4 (+/−0.9) (UHH) | 76.5 (+/−1.9) (Pass) |

TABLE 8-continued

| Polymer Ex. No. | Polymer Solids (wt. %) | Auxiliary Thickener (wt. %) | Viscosity (mPa·s) | Clarity (% T) | Stiffness (N) @ 50% RH | HHSCR (%) after 8 hrs |
|---|---|---|---|---|---|---|
| 6 | 2 | 0.0 | 5,800 | 90.7 | 9.0 (+/−0.5) (UHH) | 80.5 (+/−2.3) (Pass) |
|   | 2 | 0.6 | 22,850 | 94.1 | 10.4 (+/−0.7) (UHH) | 75.3 (+/−0.7) (Pass) |
| 6 | 3 | 0.0 | 9,200 | 91.4 | 10.7 (+/−0.7) (UHH) | 81.4 (+/−3.4) (Pass) |
|   | 3 | 0.6 | 25,250 | 93.7 | 11.8 (+/−1.1) (UHH) | 78.5 (+/−4.2) (Pass) |
| 6 | 4 | 0.0 | 13,700 | 94.1 | 12.2 (+/−0.8) (UHH) | 81.3 (+/−4.8) (Pass) |
|   | 4 | 0.6 | 30,350 | 92.2 | 14.8 (+/−0.9) (UHH) | 78.7 (+/−3.9) (Pass) |
| 6 | 5 | 0.0 | 17,400 | 93.8 | 14.0 (+/−0.3) (UHH) | 83.8 (+/−4.2) (Pass) |

HH = Hard Hold
UHH = Ultra Hard Hold

Example 20

Hair styling gel compositions containing the polymer of Example 1 are identically formulated as described in Example 18 except that various anionic thickeners (INCI: Carbomer, Acrylates/C10-30 Alkyl Acrylate Crosspolymer, Acrylates Copolymer, Acrylates/Beheneth-25 Methacrylate Copolymer) and an auxiliary fixative polymer (INCI: Polyacrylate-14) to obtain an ultra hard hold stiffness style with good humidity resistance at 90% RH. The data in Table 9 and 10 demonstrates good compatibility and stiffness synergy with various anionic thickeners (the standard deviation for the reported data is also set forth in the table).

TABLE 9

| Polymer Ex. 1 (wt. % T.S.) | 1.0 | 4.0 | 1.0 | 4.0 | 1.0 | 4.0 | 1.0 | 4.0 |
|---|---|---|---|---|---|---|---|---|
| Auxiliary Thickener | | | | | | | | |
| Carbopol ® Ultrez 21 Polymer (wt. %) | 0.6 | 0.6 | — | — | — | — | — | — |
| Carbopol ® Ultrez 20 Polymer (wt. %) | — | — | 0.6 | 0.6 | — | — | — | — |
| Carbopol ® Ultrez 10 Polymer (wt. % T.S.) | — | — | — | — | 0.6 | 0.6 | — | — |
| Carbopol ® 980 Polymer (wt. %) | — | — | — | — | — | — | 0.6 | 0.6 |
| Styling Gel Properties | | | | | | | | |
| Clarity (% T) | 94.5 | 92.2 | 93 | 90 | 90.3 | 86 | 90 | 86 |
| Viscosity (mPa·s) | 21,750 | 30,350 | 25,400 | 46,200 | 22,250 | 25,850 | 17,050 | 21,750 |
| Brookfield Yield Value (dynes/cm²) | 1,940 | 2,820 | 2,280 | 3,180 | 1,480 | 2,160 | 1,380 | 1,920 |
| Stiffness (N) @ 50% RH | 7.4 (+/−0.9) (UHH) | 14.8 (+/−0.9) (UHH) | — | — | — | — | 7.8 (+/−0.6) (UHH) | 15.3 (+/−0.8) (UHH) |
| HHSCR (%) after 8 hrs | 76.5 (+/−1.9) (Pass) | 78.7 (+/−3.9) (Pass) | — | — | — | — | 66.3 (+/−3.3) | 77.1 (+/−2.4) (Pass) |

UHH = Ultra Hard Hold

TABLE 10

| Polymer Ex. 1 (wt. % T.S.) | 2.0 | 2.0 | 2.0 | 2.0 | 4.0 | 4.0 | 4.0 | 4.0 |
|---|---|---|---|---|---|---|---|---|
| Auxiliary Thickener | | | | | | | | |
| Carbopol ® Ultrez 21 Polymer (wt. % T.S.) | 0.6 | — | — | — | 0.6 | — | — | — |

TABLE 10-continued

| Polymer Ex. 1 (wt. % T.S.) | 2.0 | 2.0 | 2.0 | 2.0 | 4.0 | 4.0 | 4.0 | 4.0 |
|---|---|---|---|---|---|---|---|---|
| Carbopol ® Aqua SF-1 Polymer (wt. % T.S.) | — | 0.6 | — | — | — | 0.6 | — | — |
| Novethix ™ L-10 Polymer (wt. % T.S.) | — | — | 0.6 | — | — | — | 0.6 | — |
| Auxiliary Fixative | | | | | | | | |
| Fixate ™ PLUS Polymer (wt. % T.S.) | — | — | — | 0.6 | — | — | — | 0.6 |
| Styling Gel Properties | | | | | | | | |
| pH | 7.0 | 7.0 | 7.0 | 7.0 | 7.0 | 7.0 | 7.0 | 7.0 |
| Viscosity (mPa·s) | 22,850 | 8,750 | 23,750 | 22,000 | 30,350 | 16,500 | 26,300 | 26,450 |
| Brookfield Yield Value (dynes/cm$^2$) | 2,220 | 750 | 3,040 | 1,530 | 2,820 | 1,400 | 2,280 | 1,960 |
| Clarity (% Transmittance) | 94.1 | 89.8 | 90.8 | 89.2 | 92.2 | 92.4 | 90.2 | 85.4 |
| Stiffness (N) @ 50% RH | 10.4 (±0.7) (UHH) | 9.1 (±0.31) (UHH) | 7.6 (±0.6) (UHH) | 7.9 (±0.8) (UHH) | 14.8 (±0.9) (UHH) | 12.2 (+/−1.8) (UHH) | 10.8 (+/−0.4) (UHH) | 10.9 (+/−0.4) (UHH) |
| HHSCR (%) after 8 hrs | 75.3 (±0.7) (Pass) | 82.6 (±2.8) (Pass) | 77.2 (±4) (Pass) | 83.9 (±3.6) (Pass) | 78.7 (±3.9) (Pass) | 83.7 (±4) (Pass) | 77.1 (±4.7) (Pass) | 78.5 (±3.9) (Pass) |

UHH = Ultra Hard Hold

Example 21

The polymer of Example 1 is formulated into a conditioning hair gel composition containing a conditioning agent. The polymer is formulated at a 1 wt. % total polymer solids for a medium hold conditioning hair styling gel and at 4 wt. % total polymer solids for an ultra stiff hold conditioning hair styling gel. The polymer is formulated into the styling gels containing the ingredients set forth in Table 11.

TABLE 11

| Component No. | Component | Amount (wt. %) | Function | INCI Name |
|---|---|---|---|---|
| 1 | Deionized Water | Q.S. | Diluent | |
| 2 | Carbopol ® Ultrez 21 Polymer | 0.6 | Auxiliary Thickener | Acrylates/C10-30 Alkyl Acrylate Crosspolymer |
| 3 | Polymer (30% active polymer solids) | 1 wt. % (medium hold) or 4 wt. % (ultra hold) | Fixative/Thickener | |
| 4 | Conditioner | 0.3 | Conditioner/Solubilizer | Panthenol or PEG-12 Dimethicone |
| 5 | Glydant ® Plus Liquid | 0.3 | Preservative | DMDM Hydantoin (and) Iodopropynyl Butylcarbamate |
| 6 | AMP-95 ® | Q.S. | Neutralizer | Aminomethyl Propanol |

Deionized water is added into a 500 gram vessel and component No. 2 is sprinkled onto the surface of the D.I. water and allowed to wet. Once the powdered auxiliary thickener is wetted, the contents of the vessel are gently mixed. Component No. 3 is added into the mixture with agitation until homogenous. Component Nos. 4 and 5 are added, followed by neutralization with the component No. 6 to a pH of 7. The composition is mixed until a clear and homogeneous composition is attained. After resting the hair gel composition for 24 hrs. to reach equilibrium, viscosity, yield value, and clarity are measured and recorded. The results are presented in Table 12.

TABLE 12

| | Medium Stiffness (1 wt. % TS) | | Ultra Stiffness (4 wt. % TS) | |
|---|---|---|---|---|
| | Panthenol | PEG-12 Dimethicone | Panthenol | PEG-12 Dimethicone |
| pH | 7.0 | 7.0 | 7.0 | 7.0 |
| Viscosity (mPa·s) | 22,550 | 22,150 | 35,100 | 33,400 |
| Yield Value (dynes/cm$^2$) | 1,970 | 1,490 | 2,870 | 2,240 |
| Clarity (% T) | 96.3 | 95.1 | 94.5 | 95.1 |

Example 22

The polymer of Example 1 is formulated into a moisturizing hair gel composition containing the components set forth in Table 13. The composition is formulated at 1 wt. % and 4 wt. % total polymer solids (T.S.) as in Example 21 except that the moisturizing agents are used in place of the conditioners. Rheology and clarity data for each composition are set forth in Table 14.

TABLE 13

| Component No. | Component | Amount (wt. %) | Function | INCI Name |
|---|---|---|---|---|
| 1 | Deionized Water | Q.S. | Diluent | |
| 2 | Carbopol ® Ultrez 21 Polymer | 0.6 | Auxiliary Thickener | Acrylates/C10-30 Alkyl Acrylate Crosspolymer |
| 3 | Polymer (30% active polymer solids) | 1 wt. % (medium hold) or 4 wt. % (ultra hold) | Fixative/Thickener | |

TABLE 13-continued

| Component No. | Component | Amount (wt. %) | Function | INCI Name |
|---|---|---|---|---|
| 4 | Moisturizing Agent | 5.0 | Moisturizer | Glycerine, Sorbitol, Propylene Glycol |
| 5 | Glydant ® Plus Liquid | 0.3 | Preservative | DMDM Hydantoin (and) Iodopropynyl Butylcarbamate |
| 6 | AMP-95 ® | Q.S. | Neutralizer | Aminomethyl Propanol |

TABLE 14

| | Medium Stiffness (1% TS) | | | Ultra stiffness (4% TS) | | |
|---|---|---|---|---|---|---|
| | Glycerine | Sorbitol | Propylene glycol | Glycerine | Sorbitol | Propylene glycol |
| pH | 7 | 7 | 7 | 7 | 7 | 7 |
| Viscosity (mPa·s) | 24,400 | 24,750 | 22,100 | 38,250 | 37,000 | 33,700 |
| Yield Value (dynes/cm²) | 2,060 | 1,980 | 1,720 | 2,960 | 2,850 | 2,630 |
| Clarity (% T) | 99.4 | 99.7 | 97.3 | 89.7 | 89 | 90.4 |

Example 23

The polymer of Example 1 is formulated into a hydro-alcoholic hair gel composition prepared from the components set forth in Table 15. The formulating procedure of Example 22 is followed except that the auxiliary diluent (absolute ethanol) is used in place of the moisturizers. The polymer is formulated at a 1 wt. % total polymer solids for a medium hold hydro-alcoholic hair styling gel and at 4 wt. % total polymer solids for an ultra stiff hold hydro-alcoholic hair styling gel. Rheology and clarity data for each composition are set forth in Table 16.

TABLE 15

| Component No. | Component | Amount (wt. %) | Function | INCI Name |
|---|---|---|---|---|
| 1 | Deionized Water | Q.S. | Diluent | |
| 2 | Carbopol ® Ultrez 21 Polymer | 0.6 | Auxiliary Thickener | Acrylates/C10-30 Alkyl Acrylate Crosspolymer |
| 3 | Polymer (30% active polymer solids) | 1 wt. % (medium hold) or 4 wt. % (ultra hold) | Fixative/Thickener | |
| 4 | Ethanol (absolute) | 15.0 | Diluent | Ethanol |
| 5 | Glydant ® Plus Liquid | 0.3 | Preservative | DMDM Hydantoin (and) Iodopropynyl Butylcarbamate |
| 6 | AMP-95 ® | Q.S. | Neutralizer | Aminomethyl Propanol |

TABLE 16

| | Medium stiffness (1 wt. % T.S.) | Ultra stiffness (4 wt. % T.S.) |
|---|---|---|
| pH | 7.1 | 6.9 |
| Viscosity (mPa·s) | 16,400 | 19,000 |
| Yield Value (dynes/cm²) | 1,110 | 1,540 |
| Clarity (% T) | 98.5 | 84.7 |

Example 24

The polymers of Examples 1 and 14 are formulated into a long lasting hair cream styling composition containing a conditioner, a sheen enhancer, and a humectant as shown in Table 17.

TABLE 17

| Component No. | Component | Amount (wt. %) | Function | INCI Name |
|---|---|---|---|---|
| 1 | Deionized Water | Q.S. | Diluent | |
| 2 | Carbopol ® Ultrez 21 Polymer | 0.6 | Auxiliary Thickener | Acrylates/C10-30 Alkyl Acrylate Crosspolymer |
| 3 | Polymer (30% active polymer solids) | 2.0 | Fixative/Thickener | |
| 4 | Conditioner | 0.3 | Conditioner | Polyquaternium-11 |
| 5 | Timiron Pigment | 0.3 | Pearlizing Agent | |
| 6 | Murumuru Butter | 0.25 | Sheen Enhancer | |
| 7 | Sorbitol | 0.6 | Humectant | Sorbitol |
| 8 | Glydant ® Plus Liquid | 0.3 | Preservative | DMDM Hydantoin (and) Iodopropynyl Butylcarbamate |
| 9 | AMP-95 ® | Q.S. | Neutralizer | Aminomethyl Propanol |

Deionized water is added into a 500 g vessel and component No. 2 is sprinkled onto the surface of the D.I. water and allowed to wet. Once the powdered auxiliary thickener is wetted, the contents of the vessel are gently mixed. Component No. 3 is added into the mixture with agitation until homogenous. Component Nos. 4 to 8 are mixed in a separate vessel until a uniform mixture is obtained and then combined with the contents of the 500 g vessel. The composition is neutralized with component No. 9 to pH 7 and mixed until a clear and homogeneous composition is attained.

Example 25

The polymer of Example 1 is formulated into a hair gel composition utilizing the components set forth in Table 18.

TABLE 18

| Component | Trade Name | Amount (wt. %) | Function | INCI Name |
|---|---|---|---|---|
| 1 | Deionized Water | Q.S. | Diluent | |
| 2 | Carbopol ® Ultrez 21 Polymer | 0.6 | Auxiliary Thickener | Acrylates/C10-30 Alkyl Acrylate Crosspolymer |
| 3 | Polymer (Ex. 1) | 2.0 | Fixative/Thickener | |
| 4 | Glydant ® Plus Liquid | 0.3 | Preservative | DMDM Hydantoin (and) Iodopropynyl Butylcarbamate |
| 5 | EDTA | 0.02 | Chelating Agent | |
| 6 | AMP-95 ® | Q.S. to 7.5 | Neutralizer | Aminomethyl Propanol |

The formulating procedure of Example 22 is followed except that the chelating agent is used in place of the moisturizing agent. Two commercially available fixative polymers polyvinylpyrrolidone (PVP) and polyvinylpyrrolidone/vinylacetate copolymer (PVP/VA) at 2.0 wt. % total active polymer solids are identically formulated and tested against the invention formulation for polymer residue utilizing the flaking evaluation test methodology and rating system described above. The evaluation results are set forth in Table 19.

TABLE 19

| Combing Repetitions | Polymer Ex. 1 | | | PVP | | | PVP/VA | | |
|---|---|---|---|---|---|---|---|---|---|
| Rating | 1 | 5 | 10 | 1 | 5 | 10 | 1 | 5 | 10 |
| 5 | x | | | | | | | | |
| 4 | | x | x | x | | | | | |
| 3 | | | | | x | | x | | |
| 2 | | | | | | x | | | x |
| 1 | | | | | | x | | | |
| 0 | | | | | | | | | x |

Example 26

This example illustrates the preparation of mascara compositions utilizing the polymers of Examples 1, 7, and 13. The mascara composition is formulated from the components set forth in Table 20.

TABLE 20

| Part | Component No. | INCI (Trade Name) | Wt. % | Function |
|---|---|---|---|---|
| A | 1 | Beeswax (Beeswax White Pure, batch #481) | 5.0 | Structurant |
| | 2 | Copernicia Cerifera (Carnauba) Wax (Carnauba Wax T1, batch #161) | 5.0 | Structurant |
| | 3 | Euphorbia Cerifera (Candelilla) Wax (Candelilla Wax Refined) | 3.0 | Structurant |
| | 4 | Steric acid | 2.0 | Emulsifier |
| | 5 | Glyceryl Stearate (Geleol) | 5.0 | Emulsifier |
| | 6 | Isopropyl Myristate (Crodamol IPM) | 3.0 | Emollient |
| | 7 | Petrolatum | 4.0 | Emollient |
| | 8 | Iron Oxides/CI 77499 (Iron Oxide Black 34-PC-3069) | 12.0 | Pigment |
| B | 9 | Phenoxyethanol, Methyl-, Butyl-, Ethyl-, Propyl-, Isobutylparaben (Phenonip) | 0.9 | Preservative |
| | 10 | Cyclopentasiloxane (Dow Corning ® 245 Fluid) | 3.0 | Emollient |
| | 11 | PEG-12 Dimethicone (Dow Corning ® 193 Surfactant) | 0.5 | Plasticizer |
| | 12 | DI Water | 41.0 | Diluent |
| | 13 | Polymer (Examples 1, 7, and 13) 3.5% total active solids (T.S.) | 11.0 | Film Former |
| | 14 | Triethanolamine (99%) in water | Q.S. to 7.5 | Neutralizer |

The Part A components (except the pigment) are added to a mixing vessel and heated to 85° C. while mixing. The pigment is then added and mixed into the oil phase. The Part A batch is cooled and then the Part B components are added to the batch as follows: component Nos. 9, 10 and 11 are added in the order listed and mixed. The polymer component No. 13 and D.I. water component No. 12 are separately mixed until homogeneous and then added to the Part AB master batch and uniformly mixed. The batch is adjusted with triethanolamine to a pH of 7.5.

What is claimed is:

1. A hair fixative gel comprising:
   A) a crosslinked acrylic copolymer polymerized from a monomer composition comprising:
   a) from about 10% to about 80% by weight of a first monomeric component selected from one or more ethylenically mono-unsaturated monomers containing at least one carboxylic acid group;
   b) from about 90% to about 15% by weight of a second ethylenically mono-unsaturated monomeric component selected from at least one linear or branched $C_1$ to $C_5$ alkyl ester of (meth)acrylic acid, at least one $C_1$ to $C_5$ hydroxyalkyl ester of (meth)acrylic acid, and mixtures thereof;
   c) from about 0.01% to about 5% by weight of crosslinking component comprising a first polyunsaturated crosslinking monomer and a second polyunsaturated crosslinking monomer, wherein said first crosslinking monomer is selected from at least one polyfunctional acrylate having at least two polymerizable ethylenically unsaturated double bonds and said second crosslinking monomer is selected from at least one polyalkenyl polyether having at least two polymerizable ethylenically unsaturated double bonds; and optionally
   d) from about 1% to about 35% by weight of at least one other ethylenically mono-unsaturated monomer component different from monomeric components a) and b), wherein all monomer weight percentages are based on the weight of the total monomer composition;
   B) water; and
   C) a neutralizer.

2. A hair fixative gel of claim 1, wherein said first crosslinking monomer is selected from the esterification product of (meth)acrylic acid and a linear or branched polyol having 2 to 12 carbon atoms.

3. A hair fixative gel of claim 2, wherein said polyol is selected from alkylene glycol, polyalkylene glycol, trimethylolethane and dimers thereof, trimethylolpropane and dimers thereof, triethylolpropane and dimers thereof, tetramethylolmethane (pentaerythritol), dipentaerythritol, and mixtures thereof.

4. A hair fixative gel of claim 3, wherein said esterification product contains 2 to 6 unsaturated ester groups per molecule.

5. A hair fixative gel of claim 1, wherein said second crosslinking monomer is selected from the etherification product of allyl alcohol and a linear or branched polyol having 2 to 12 carbon atoms.

6. A hair fixative gel of claim 2, wherein said polyol is selected from sucrose, pentaerythritol, dipentaerythritol, trimethylolethane and dimers thereof, trimethylolpropane and dimers thereof, triethylolpropane and dimers thereof, and mixtures thereof.

7. A hair fixative gel of claim 6, wherein said etherification product contains 2 to 8 alkyl groups per molecule.

8. A hair fixative gel of claim 1, wherein said at least one other ethylenically mono-unsaturated monomeric component is selected from a monomer represented by the formulas:

$$CH_2=C(R)C(O)OR^1, \quad (d1)$$

wherein R is selected from hydrogen or methyl; and $R^1$ is selected from $C_6$-$C_{10}$ alkyl, $C_6$ to $C_{10}$ hydroxyalkyl, $-(CH_2)_2 OCH_2CH_3$, and $-(CH_2)_2C(O)OH$

$$CH_2=C(R)X, \quad (d2)$$

wherein R is hydrogen or methyl; and X is selected from $-C_6H_5$, $-CN$, $-C(O)NH_2$, $-NC_4H_6O$, $-C(O)NHC(CH_3)_3$, $-C(O)N(CH_3)_2$, $-C(O)NHC(CH_3)_2(CH_2)_4CH_3$, and $-C(O)NHC(CH_3)_2CH_2S(O)(O)OH$;

$$CH_2=CHOC(O)R^1, \quad (d3)$$

wherein $R^1$ is linear or branched $C_1$-$C_{18}$ alkyl; and

$$CH_2=C(R)C(O)OAOR^2, \quad (d4)$$

wherein A is a divalent radical selected from $-CH_2CH(OH)CH_2-$ and $-CH_2CH(CH_2OH)-$, R is selected from hydrogen or methyl, and $R^2$ is an acyl residue of a linear or branched, saturated or unsaturated $C_{10}$ to $C_{22}$ fatty acid.

9. A hair fixative composition of any of claims 1 to 8, wherein the weight ratio of said first crosslinking monomer to said second crosslinking monomer ranges from about 1:100 to about 100:1.

10. A hair fixative composition of any of claims 1 to 9, wherein said first crosslinking monomer is selected from ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, trimethylolpropane tri(meth)acrylate, trimethylolethane tri(meth)acrylate, tetramethylolmethane tri(meth)acrylate, ditrimethylolpropane tetra(meth)acrylate, tetramethylolmethane tetra(meth)acrylate, pentaerythritol tetra(meth)acrylate; dipentaerythritol hexa(meth)acrylate and mixtures thereof.

11. A hair fixative composition of any of claims 1 to 10, wherein said second crosslinking monomer is selected from polyallyl ethers of sucrose having from 2 to 8 alkyl groups per molecule, pentaerythritol diallyl ether, pentaerythritol triallyl ether, and pentaerythritol tetraallyl ether; trimethylolpropane diallyl ether, trimethylolpropane triallyl ether, and mixtures thereof.

12. A hair fixative gel of any of claims 1 to 11, wherein said crosslinked acrylic copolymer has an specific viscosity ranging from about 1 to about 8.

13. A hair fixative gel of any of claims 1 to 12, having a clarity (% transmittance) greater or equal to 80 percent.

14. A hair fixative gel of any of claims 1 to 13 having a Brookfield viscosity value of at least 8,000 mPa·s.

15. A hair fixative gel of any of claims 1 to 14, wherein said crosslinked acrylic copolymer is the only fixative and thickener contained in said composition.

16. A hair fixative gel of any of claims 1 to 14, further containing an auxiliary thickener, an auxiliary fixative, and combinations thereof.

17. A hair fixative gel of claim 16, wherein said auxiliary thickener is an anionic polymer.

18. A hair fixative gel of claim 17, wherein said auxiliary thickener is selected from a Carbomer, Acrylates/C10-30 Alkyl Acrylate Crosspolymer, Acrylates Copolymer, Acrylates/Beheneth-25 Methacrylate Copolymer, and mixtures thereof.

19. A hair fixative gel of claim 17, wherein said anionic polymer is in powdered form.

20. A hair fixative gel of any of claim 1 to 14, 16, 17, 18, or 19 further containing a at least one component selected from, hair conditioning agents, fragrance(s), fragrance solubilizer(s), emollients, emulsifiers, moisturizers, vitamins, hair growth promoters, hair sheen enhancer(s), particulates, gas bubbles, moisturizers, pH adjusting agents, chelating agents, buffering agents, botanical extract(s), hair colorants, insoluble components, thermochromic dyes, hair bleaching agents, pigments, preservatives; and combinations thereof.

21. A hair fixative gel of any of claims 1 to 20, wherein said first monomeric component in said monomer composition is (meth)acrylic acid.

22. A hair fixative gel of any of claims 1 to 21, wherein said second monomeric component in said monomer composition is a linear or branched $C_1$ to $C_5$ alkyl(meth)acrylate.

23. A hair fixative gel of any of claims 1 to 22, wherein said second monomer component in said monomer composition is ethyl acrylate.

24. A personal care composition comprising a film former selected from a polymer comprising:
A) a crosslinked acrylic copolymer polymerized from a monomer composition comprising:
a) from about 10% to about 80% by weight of a first monomeric component selected from one or more ethylenically mono-unsaturated monomers containing at least one carboxylic acid group;
b) from about 90% to about 15% by weight of a second ethylenically mono-unsaturated monomeric component selected from at least one linear or branched $C_1$ to $C_5$ alkyl ester of (meth)acrylic acid, at least one $C_1$ to $C_5$ hydroxyalkyl ester of (meth)acrylic acid, and mixtures thereof;
c) from about 0.01% to about 5% by weight of crosslinking component comprising a first polyunsaturated crosslinking monomer and a second polyunsaturated crosslinking monomer, wherein said first crosslinking monomer is selected from at least one polyfunctional acrylate having at least two polymerizable ethylenically unsaturated double bonds and said second crosslinking monomer is selected from at least one polyalkenyl polyether having at least two polymerizable ethylenically unsaturated double bonds; and optionally
d) from about 1% to about 35% by weight of at least one other ethylenically mono-unsaturated monomer component different from monomeric components a) and b), wherein all monomer weight percentages are based on the weight of the total monomer composition; and
B) a neutralizer.

25. A personal care composition of claim 24, further containing an auxiliary thickener.

26. A personal care composition of claim 25, wherein said auxiliary thickener is an anionic polymer.

27. A personal care composition of claim 26, wherein said auxiliary thickener is selected from a Carbomer, Acrylates/C10-30 Alkyl Acrylate Crosspolymer, Acrylates Copolymer, Acrylates/Beheneth-25 Methacrylate Copolymer, and mixtures thereof.

28. A personal care composition of any of claims 24 to 27, further comprising a component selected from a pigment, a UV absorber, a moisturizer, an emulsifier, an emollient, a pH adjusting agent, a chelating agent, a buffering agent, botanical extract(s), a preservative; and combinations thereof.

29. A personal care composition of any of claims 24 to 28, which is a cosmetic formulation.

* * * * *